(12) United States Patent
Cronstein et al.

(10) Patent No.: US 9,381,245 B2
(45) Date of Patent: Jul. 5, 2016

(54) METHODS FOR INHIBITING OSTEOLYSIS

(71) Applicants: Bruce N Cronstein, New York, NY (US); Kathryn J Moore, Westfield, NJ (US); Aranzazu Mediero-Munoz, New York, NY (US); Bhama Ramkhelawon, New York, NY (US)

(72) Inventors: Bruce N Cronstein, New York, NY (US); Kathryn J Moore, Westfield, NJ (US); Aranzazu Mediero-Munoz, New York, NY (US); Bhama Ramkhelawon, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/058,392

(22) Filed: Oct. 21, 2013

(65) Prior Publication Data

US 2014/0112939 A1    Apr. 24, 2014

Related U.S. Application Data

(60) Provisional application No. 61/715,991, filed on Oct. 19, 2012.

(51) Int. Cl.
| | |
|---|---|
| *A61K 39/395* | (2006.01) |
| *A61K 45/06* | (2006.01) |
| *A61K 31/713* | (2006.01) |
| *A61K 38/16* | (2006.01) |
| *A61K 38/18* | (2006.01) |

(52) U.S. Cl.
CPC ............... *A61K 45/06* (2013.01); *A61K 31/713* (2013.01); *A61K 38/16* (2013.01); *A61K 38/18* (2013.01)

(58) Field of Classification Search
None
See application file for complete search history.

(56) References Cited

U.S. PATENT DOCUMENTS

| | | | | |
|---|---|---|---|---|
| 6,051,587 | A * | 4/2000 | Dakashinamurti et al. | ... 514/345 |
| 6,326,359 | B1 | 12/2001 | Monaghan et al. | |
| 7,226,913 | B2 | 6/2007 | Linden et al. | |
| 2003/0229137 | A1* | 12/2003 | Chen et al. | ..................... 514/456 |
| 2004/0064039 | A1 | 4/2004 | Belardinelli | |
| 2005/0020915 | A1 | 1/2005 | Belardinelli et al. | |
| 2005/0171050 | A1 | 8/2005 | Dobson | |
| 2005/0182018 | A1 | 8/2005 | Linden et al. | |
| 2005/0261236 | A1 | 11/2005 | Okusa et al. | |
| 2006/0019896 | A1* | 1/2006 | Li et al. | ........................... 514/12 |
| 2006/0034941 | A1 | 2/2006 | Dobson | |
| 2006/0100169 | A1 | 5/2006 | Rieger et al. | |
| 2007/0225247 | A1 | 9/2007 | Zablocki et al. | |
| 2011/0256544 | A1 | 10/2011 | Kolodkin et al. | |

FOREIGN PATENT DOCUMENTS

| | | |
|---|---|---|
| WO | 0224142 | 3/2002 |
| WO | 2012042289 | 4/2012 |
| WO | 2012047706 | 4/2012 |

OTHER PUBLICATIONS

Enoki et al. Netrin-4 derived from murine vascular endothelial cells inhibits osteoclast differentiation in vitro and prevents bone loss in vivo. FEBS Lett. Jun. 27, 2014;588(14):2262-9. Epub May 17, 2014.*
Osteolysis, MeSH Database, NCBI, Bethesda, Maryland [online], [retrieved on Dec. 29, 2014]. Retrieved from the Internet: <URL: http://www.ncbi.nlm.nih.gov/mesh/68010014?report=Docsum &format=text>.*
Osteoporosis, MeSH Database, NCBI, Bethesda, Maryland [online], [retrieved on Jan. 3, 2014]. Retrieved from the Internet: <URL: http://www.ncbi.nlm.nih.gov/mesh/68010024?report=Docsum &format=text>.*
Pageau SC. Denosumab. MAbs. May-Jun. 2009;1(3):210-5. Epub May 29, 2009.*
Tai et al. Transcriptional induction of cyclooxygenase-2 in osteoblasts is involved in interleukin-6-induced osteoclast formation. Endocrinology. Jun. 1997;138(6):2372-9.*
Ong, et al., "Risk of Subsequent Revision after Primary and Revision Total Joint Arthroplasty", Clin Orthop Relat Res, 2010, 468(11): 3070-6.
Mediero, et al., "Adenosine A2A Receptor Activation Prevents Wear Particle-Induced Osteolysis", Sci Transl Med, 2012; 4(135): 135-65.
Walsh, et al., "Bone remodeling in rheumatic disease: a question of balance", Immunol Rev, 2010; 233(1):301-12.
Negishi-Koga, et al., "Suppression of bone formation by osteoclastic expressionof semaphorin 4D", Nature Medicine, 2011; 17(11): 1473-80.
Hughes, A., et al., "A Class III Semaphorin (Sema3e) Inhibits Mouse Osteoblast Migration and Decreases Osteoclast Formation In Vitro", Calcified Tissue International, 2012; 90(2): 151-62.
Hayashi, et al., "Osteoprotection by semaphorin 3A", Nature, 2012; 485(7396): 69-74.
Sutton, et al., "Semaphorin 3B is a 1,25-Dihydroxyvitamin D3-Induced Gene in Osteoblasts that Promotes Osteoclastogenesis and Induces Osteopenia in Mice", Molecular Endocrinology, 2008; 22(6): 1370-81.

(Continued)

*Primary Examiner* — David Romeo
(74) *Attorney, Agent, or Firm* — Klauber & Jackson LLC

(57) ABSTRACT

The invention provides methods and compositions for reducing or inhibiting osteolysis, bone resorption, osteoclast differentiation and stimulation and the loosening of medical prostheses by administering a compound or agent that inhibits the biological activity of an axon guidance protein. The compound or agent my inhibit transcription or translation of or bind to an axon guidance protein, such as, for instance, a netrin like netrin-1. Likewise, the compound or agent may inhibit transcription or translation of or bind to a receptor of an axon guidance protein, such as, for instance, a netrin receptor such as unc5b. In some instances, the compound or agent is an agonist of an adenosine $A_{2A}$ receptor. The invention also extends to pharmaceutical compositions comprising such compounds and agents.

16 Claims, 9 Drawing Sheets

(56) References Cited

OTHER PUBLICATIONS

Tamagnone, et al., "Semaphorin pathways orchestrate osteogenesis", Nat Cell Biol, 2006, 8(6): 545-7.
Koh et al., "Association study of semaphorin 7a (sema7a) polymorphisms with bone mineral density and fracture risk in postmenopausal Korean women", J Hum Genet, 2006; 51(2): 112-7.
Togari, et al. "Expression of mRNA for axon guidance molecules, such as semaphorin-III, netrins and neurotrophins, in human osteoblasts and osteoclasts", Brain Research, 2000; 878(1-2): 204-9.
Giordano, et al., "The Semaphorin 4D receptor controls invasive growth by coupling with Met", Nat Cell Biol, 2002; 4 (9): 720-4.
Sierra, et al., "Tumor angiogenesis and progression are enhanced by Sema4D produced by tumor-associated macrophages", J Exp Med, 2008; 205(7): 1673-85.
Kara, et al., "Adenosine A1 Receptors (A1R) Regulate Bone Resorption II Adenosine A1R Blockade or Deletion Increases Bone Density and Prevents Ovariectomy-Induced Bone Loss", Arthritis Rheum, 2010, 62(2): 534-41.
Kara, et al., "Adenosine A1 receptors (A1Rs) play a critical role in osteoclast formation and function", FASEB J, 2010, 24(7): 2325-33.
Lomaga, et al., "TRAF6 deficiency results in osteopetrosis and defective interleukin-1, CD40, and LPS signaling", Genes Dev, 1999, 13(8): 1015-24.
Kim, N., et al., "Osteoclast differentiation independent of the TRANCE-RANK-TRAF6 axis", J Exp Med, 2005, 202(5): 589-95.
Naito, et al., "Severe osteopetrosis, defective interleukin-1 signalling and lymph node organogenesis in TRAF6-deficient mice", Genes Cells, 1999, 4(6): 353-62.
Mediero, et al., "Adenosine A2A Receptor Ligation Inhibits Osteoclast Formation", The American Journal of Pathology, 2012; 180(2): 775-86.
Merrill, et al., "Denosine A, Receptor Promotion of Multinucleated Giant Cell Formation by Human Monocytes", Arth. Rheum., 1997, 40: 1308-1315.
Gharibi, et al., Contrasting effects of A1 and A2b adenosine receptors on adipogenesis, International Journal of Obesity, 2012, 36, 397-406.
Costa, et al., "On the Role of Subtype Selective Adenosine Receptor Agonists During Proliferation and Osteogenic Differentiation of Human Primary Bone Marrow Stromal Cells", Journal of Cellular Physiology, 2011, 226(5): 1353-66.
Russell, et al., "Adenosine Inhibition of Lipopolysaccharide-Induced Interleukin-6 Secretion by the Osteoblastic Cell Line MG-63", Calcif Tissue Int, 2007, 81(4): 316-26.
Evans, et al., "Human Osteoblast Precursors Produce Extracellular Adenosine, Which Modulates Their Secretion of IL-6 and Osteoprotegerin", J Bone Miner Res, 2006, 21(2): 228-36.
Shimegi, "Mitogenic Action of Adenosine on Osteoblast-Like Cells, MC3T3-E1", Calcif Tissue Int, 1998, 62(5): 418-25.
Takedachi, et al., "Fibroblast Growth Factor-2 Stimulates Directed Migration of Periodontal Ligament Cells via PI3K/AKT Signaling and CD44/Hyaluronan Interaction", J. Cell. Physiol, 2011, 226: 809-821.
Fu, et al., "Parathyroid Hormone Controls Receptor Activator of NF-B Ligand Gene Expression via a Distant Transcriptional Enhancer", Mol Cell Biol, 2006, 26(17): 6453-68.
Cronstein, et al., "Adenosine: A Physiological Modulator of Superoxide Anion Generation by Human Neutrophils", Journal of Experimental Medicine, 1983, 158: 1160-1177.
Cronstein, et al., "Adenosine: A Physiological Modulator of Superoxide Anion Generation by Human Neutrophils. Adenosine acts via an A2 receptor on human neutrophils", A physiologic Journal of Immunology, 1985, 135: 1366-1371.
Hasko, et al. "Adenosine receptors: therapeutic aspects for inflammatory and immune diseases", Nat Rev Drug Discov, 2008, 7(9): 759-70.
Chan, et al., "Methotrexate—how does it really work?", Nat Rev Rheumatol, 2010, 6(3): 175-8.
Suda, et al., "Role of 1a,25-dihydroxyvitamine D3 in osteoclast differentiation and function", Methods Enzymol., 1997, 282: 223-235.
Lacey, et al., "Osteoprotegerin Ligand is a Cytokine that Regulates Osteoclast Differentiation and Activation", Cell, 1988, 93: 165-176.
Shevde et al., "Estrogens suppress RANK ligand-induced osteoclast differentiation via a stromal cell independent mechanism involving c-Jun repression", Proc. Natl. Acad. Sci. U.S.A. 2000, 97: 7829-7834.
Takahashi, et al., "A new member of tumor necrosis factor ligand family, ODF/OPGL/TRANCE/RANKL, regulates osteoclast differnetiation and function" Biochem. Biophys. Res. Commun., 1999, 256: 449-455.
van Gils, et al., "The neuroimmune guidance cue netrin-1 promotes atherosclerosis by inhibiting macrophage emigration from plaques", Nat Immunol, 2012, 13(2): 136-43.
Vasudevan, et al., "Cellular Response to Prosthetic Wear Debris Differs in Rheumatoid Versus Non-Rheumatoid Arthritis Patients", Arthritis Rheum, 2012, 64(4): 1005-14.
Assaife-Lopes, et al., "Activation of Adenosine A2A Receptors Induces TrkB Translocation and Increases BDNF-Mediated Phospho-TrkB Localization in Lipid Rafts: Implications for Neuromodulation", J Neurosci, 2010, 30(25): 8468-80.
Lee, et al., "Identification of nuclear factor 1 (NF1) as a transcriptional modulator of rat A2a adenosine receptor", Molecular Brain Research, 2003,111(1-2):61-73.
Lee, et al., "Distinctive features of TrK neurotrophin receptor transactivation by G protein-coupled receptors", Cytokine Growth Factor Rev, 2002, 13(1): 11-17.
Lee, et al., "Activation of Trk neurotrophin receptors in the absence of neurotrophins", Proc Nat Acad, 2001, 98(6):3555-3560.
Wiese, et al., "Adenosine receptor A2A-R contributes to motoneuron survival by transactivating the tyrosine kinase receptor TrkB", Proc Natl Acad Sci U S A, 2007, 104(43): 17210-5.
Carroll, et al., "A2B Adenosine Receptor Promotes Mesenchymal Stem Cell Differentiation to Osteoblasts and Bone Formation in Vivo", J Biol Chem, 2012, 287(19): 15718-27.
Yu et al., "Dynamic regulation of axon guidance" Nature Neuroscience, 2001, 4: 1169-1176.
Tomita et al., "Effects of selective prostaglandin EP4 receptor antagonist on osteoclast formation and bone resorption in vitro", Bone, 2002, 30:159-163.

* cited by examiner

Sham

Particulate + saline

Particulate + CGS

Joint Arthroplasty

Revision Arthroplasty

METHODS FOR INHIBITING OSTEOLYSIS

CROSS REFERENCE TO RELATED APPLICATIONS

The present application is a claims the priority of U.S. Provisional Application Ser. No. 61/715,991, filed Oct. 19, 2012, the disclosure of which is incorporated by reference herein in its entirety, under 35 U.S.C. §119(e).

FIELD OF THE INVENTION

The present invention relates to methods and compositions for inhibiting osteolysis, osteoporosis or osteoclast activity or activating or stimulating osteoblast activity.

BACKGROUND OF THE INVENTION

Total joint replacements are commonly performed surgeries that reduce pain and improve quality of life. Indeed, every year nearly 800,000 patients will undergo hip or knee replacement surgeries in the United States (*NIAMS website*. 2012). The failure rate of hip and knee prostheses is approximately 1%/year although younger age is an important risk factor for prosthesis failure requiring revision arthroplasty (Ong, et al., *Clin Orthop Relat Res*, 2010, 468(11): 3070-6). The most common cause for prosthesis failure requiring revision is peri-implant osteolysis leading to loosening of the prosthesis. As joints are replaced in younger individuals and the elderly live longer and lead more active lives it is imperative that new approaches to bone preservation be developed to prevent a growing wave of revision surgeries with their associated morbidities, mortality and cost.

Osteolysis results from the inflammatory response to wear particles (ultra high molecular weight polyethylene particles, UHMWPE) or metal fragments leading to stimulation of osteoclast differentiation and bone resorption. In recent studies, using a murine model of wear particle-induced osteolysis, stimulation of adenosine $A_{2A}$ receptors ($A_{2A}$ receptor) dramatically reduced wear particle-induced bone resorption by diminishing M-CSF, RANKL, IL-1 and TNFα and increasing IL-10 levels in the exudate overlying the implanted wear particles and by diminishing the number of cells expressing TNFα, RANK, CD68, αSMA, RANKL and osteopontin while increasing the number of osteoprotegerin-expressing cells in the calvarial bone (Mediero, et al., *Sci Transl Med*, 2012; 4(135): 135-65). As had previously been reported, not only does the inflammatory response to UHMWPE promote a marked increase in osteoclasts but a reduction in osteoblasts as well leading to uncoupling of bone resorption from bone formation that characterizes bone homeostasis.

Although cytokine-stimulated osteoclast activation has been well described as the principal pathophysiologic mechanism mediating inflammatory bone loss there is diminished bone formation and the mechanism for this has been less well studied. Secretion of inhibitors of the Wnt-frizzled pathway, such as DKK-1, at inflamed sites is thought to inhibit osteoblast differentiation and function (Reviewed in Walsh, et al., *Immunol Rev*, 2010; 233(1):301-12). More recently axonal guidance proteins, such as semaphorin 4D (sema4D), produced by osteoclasts and activated macrophages have been reported to diminish osteoblast differentiation and function (Negishi-Koga, et al., *Nature Medicine*, 2011; 17(11): 1473-80). The role of other axonal guidance proteins in coupling or uncoupling of bone resorption and synthesis have also become a subject of interest (Hughes, A., et al., *Calcified Tissue International*, 2012; 90(2): 151-62; Hayashi, et al., *Nature*, 2012; 485(7396): 69-74; Sutton, et al., *Molecular Endocrinology*, 2008; 22(6): 1370-81; Tamagnone, et al., *Nat Cell Biol*, 2006, 8(6): 545-7; Koh, et al., *J Hum Genet*, 2006; 51(2): 112-7 and Togari, et al., *Brain Research*, 2000; 878(1-2): 204-9). In the murine calvaria model of wear particle-induced bone resorption, $A_{2A}$ receptor agonists were shown to inhibit the accumulation of sema4D-expressing cells, most of which are CD68+ macrophages, at osteolytic sites. Although the expression of sema4D on T cells and other cells has been well documented there is little evidence that macrophages express this molecule (Giordano, et al., *Nat Cell Biol*, 2002; 4(9): 720-4 and Sierra, et al., *J Exp Med*, 2008; 205(7): 1673-85).

Axon guidance (also called axon path finding) is a subfield of neural development concerning the process by which neurons send out axons to reach the correct targets. Axons often follow very precise paths in the nervous system, and how they manage to find their way so accurately is being researched. Growing axons have a highly motile structure at the growing tip called the growth cone, which "sniffs out" the extracellular environment for signals that instruct the axon which direction to grow. These signals, called guidance cues, can be fixed in place or diffusible; they can attract or repel axons. Growth cones contain receptors that recognize these guidance cues and interpret the signal into a chemotropic response. The general theoretical framework is that when a growth cone "senses" a guidance cue, the receptors activate various signaling molecules in the growth cone that eventually affect the cytoskeleton. If the growth cone senses a gradient of guidance cue, the intracellular signaling in the growth cone happens asymmetrically, so that cytoskeletal changes happen asymmetrically and the growth cone turns toward or away from the guidance cue.

A combination of genetic and biochemical methods (see below) has led to the discovery of several important classes of axon guidance molecules and their receptors. Netrins are secreted molecules that can act to attract or repel axons by binding to their receptors, DCC and UNC5. Slits also known as Sli are secreted proteins that normally repel growth cones by engaging Robo (Roundabout) class receptors. Ephrins are cell surface molecules that activate Eph receptors on the surface of other cells. This interaction can be attractive or repulsive. In some cases, Ephrins can also act as receptors by transducing a signal into the expressing cell, while Ephs act as the ligands. Signaling into both the Ephrin- and Eph-bearing cells is called "bi-directional signaling." Semaphorins occur as many types and are primarily axonal repellents, and activate complexes of cell-surface receptors called Plexins and Neuropilins. Cell adhesion molecules (CAMs) are integral membrane proteins mediating adhesion between growing axons and eliciting intracellular signalling within the growth cone. CAMs are the major class of proteins mediating correct axonal navigation of axons growing on axons (fasciculation). There are two CAM subgroups: IgSF-CAMs (belonging to the immunoglobulin superfamily) and Cadherins (Ca-dependent CAMs).

In addition, many other classes of extracellular molecules are used by growth cones to navigate properly including developmental morphogens, such as BMPs, Wnts, Hedgehog, and FGFs, extracellular matrix and adhesion molecules such as laminin, tenascins, proteoglycans, N-CAM, and L1, growth factors like NGF, and neurotransmitters and modulators like GABA.

Growing axons rely on variety of guidance cues in deciding upon a growth pathway. The growth cones of extending axons process these cues in an intricate system of signal interpretation and integration, in order to insure appropriate guidance.

Adhesive cues provide physical interaction with the substrate necessary for axon protrusion. These cues can be expressed on glial and neuronal cells the growing axon contacts or be part of the extracellular matrix. Examples are laminin or fibronectin, in the extracellular matrix, and cadherins or Ig-family cell-adhesion molecules, found on cell surfaces. Tropic cues act as attractants or repellents and cause changes in growth cone motility by acting on the cytoskeleton through intracellular signaling. For example, Netrin plays a role in guiding axons through the midline, acting as both an attractant and a repellent. While Semaphorin3A, helps axons grow from the olfactory epithelium to map different locations in the olfactory bulb. Modulatory cues influence the sensitivity of growth cones to certain guidance cues. For instance, neurotrophins can make axons less sensitive to the repellent action of Semaphorin3A.

Given the abundance of these different guidance cues it was previously believed that growth cones integrate various information by simply summing the gradient of cues, in different valences, at a given point in time, to making a decision on the direction of growth. However, studies in vertebrate nervous systems of ventral midline crossing axons, has shown that modulatory cues play a crucial part in tuning axon responses to other cues, suggesting that the process of axon guidance is nonlinear. For examples, commisurial axons are attracted by netrin and repelled by slit. However, as axons approach the midline, the repellent action of Slit is suppressed by Robo-3/Rig-1 receptor. Once the axons cross the midline, activation of Robo by Slit silences Netrin-mediated attraction, and the axons are repelled by Slit.

The netrin family is composed mostly of secreted proteins which serve as bifunctional signals: attracting some neurons while repelling others during the development of brain. Expressed in the midline of all animals possessing bilateral symmetry, they can act as long or short range signals during neurogenesis. In order to carry out their functions, netrins interact with specific receptors: DCC or UNC-5 depending on whether they are trying to attract or repel neurons respectively. There is a high degree of conservation in the secondary structure of netrins, which has several domains which are homologous with laminin at the amino terminal end. The C-terminal domain is where most of the variation is found between species and contains different amino acids which allow interaction with specific proteins in extracellular matrix or on cell surface. The differences in terms of structure and function have led to the identifications of several different types of netrins including netrin-1, netrin-3, and netrins-G.

Netrin-1 is found in the floor plate and neuroepithelial cells of the ventral region of the spinal cord, as well as other locations in the nervous system including the somatic mesoderm, pancreas and cardiac muscle. Its main role is in axonal guidance, neuronal migration and morphogenesis of different branching structures. Mice with mutations in the netrin-1 gene were observed to be lacking in forebrain and spinal cord commissural axons. Netrin-3 is different from other netrins. While expressed during development of the peripheral nervous system in the motor, sensory and sympathetic neurons, it is very limited in the central nervous system. Studies with netrin-3 have noticed a reduced ability to bind with DCC receptors when compared with netrin-1. This suggests that it mainly operates through other receptors. Netrins-G are secreted but remain bound to the extracellular surface of the cell membrane through Glycophosphatidylinositol (GPI). They are expressed predominantly in the central nervous system in places such as the thalamus and mitral cells of the olfactory bulb.[7] They do not bind to DCC or UNC-5 and instead bind to ligand NGL-1, which results in an intracellular transduction cascade. The two versions, netrins-G1 and netrins-G2, are found only in vertebrates. It is believed that they evolved independently of other netrins in order to facilitate the construction of the brain.

DCC and UNC-5 proteins carefully mediate netrin-1 responses. The UNC-5 protein is mainly involved in signaling repulsion. DCC, which is implicated in attraction, can also serve as a co-factor in repulsion signaling when far away from the source of netrin-1. DCC is highly expressed in the central nervous system and associated with the basal lamina of epithelia cells. In the absence of netrin-1, these receptors are known to induce apoptosis.

SUMMARY OF THE INVENTION

The invention relates to the application and use of modulators of axonal guidance, including antagonists or inhibitors of axonal guidance proteins, to inhibit osteolysis, osteoporosis or osteoclast activity or to stimulate or enhance osteoblast activity.

In a first aspect, the invention provides a method for inhibiting, reducing or slowing osteolysis or osteoporosis by inhibiting, inhibiting the biological activity of or antagonizing an axonal guidance protein. The method may feature administering to a subject a therapeutically effective amount of an agent effective to inhibit or reduce the biological activity of an axonal guidance protein or a receptor of the axonal guidance protein, or an analog, derivative or combination thereof.

In a second aspect, the invention provides a method for inhibiting osteoclast differentiation, activation or activity by inhibiting, inhibiting the biological activity of or antagonizing an axonal guidance protein. The method may feature administering to a subject a therapeutically effective amount of an agent effective to inhibit or reduce the biological activity of an axonal guidance protein or a receptor of the axonal guidance protein, or an analog, derivative or combination thereof.

In a third aspect, the invention provides a method for increasing or promoting bone density by inhibiting, inhibiting the biological activity of or antagonizing an axonal guidance protein. The method may feature administering to a subject a therapeutically effective amount of an agent effective to inhibit or reduce the biological activity of an axonal guidance protein or a receptor of the axonal guidance protein, or an analog, derivative or combination thereof. The method may further feature inhibiting osteoclast differentiation, activation or activity, or the method may further feature stimulating osteoblast differentiation, activation or activity.

In a fourth aspect, the invention provides a method for treating a disease caused all or in part by or characterized by osteolysis, reduced bone density or undesired osteoclast activity. The method features increasing or promoting bone density by inhibiting, inhibiting the biological activity of or antagonizing an axonal guidance protein. The method may feature administering to a subject a therapeutically effective amount of an agent effective to inhibit or reduce the biological activity of an axonal guidance protein or a receptor of the axonal guidance protein, or an analog, derivative or combination thereof. The disease may be, for instance, one of osteoporosis, an inflammatory disease of bone, a metabolic bone disease or a metastatic bone disease, for example, multiple myeloma. The method may further feature inhibiting osteoclast differentiation, activation or activity, or the method may further feature stimulating osteoblast differentiation, activation or activity. The method may further feature inhibiting osteoclast differentiation, activation or activity, or the method may further feature stimulating osteoblast differentiation, activation or activity.

For each of these four aspects, the axonal guidance protein may be, for instance, one of sema4D, plexin A1, and netrin-1. Also, for each of these four aspects the agent effective to inhibit or reduce the biological activity of an axonal guidance protein or a receptor of the axonal guidance protein, such as for instance netrin-1 or its receptor unc5b, may be, for instance, an antibody, a peptide, a nucleic acid, for instance, an interfering RNA such as siRNA, or a small molecule.

In some instances the agent effective to inhibit or reduce the biological activity of an axonal guidance protein or a receptor of the axonal guidance protein, or an analog, derivative or combination thereof, may be administered in combination with one or more drugs useful in inhibiting bone resorption or inhibiting differentiation or stimulation of osteoclasts or a combination of any of these agents. Such other compounds may be, for instance, anti-inflammatory compounds, bisphosphonates or growth factors.

In a fifth aspect, the present invention provides a method for inhibiting, reducing the biological activity of or antagonizing an axonal guidance protein by administering an adenosine receptor agonist such as, for instance, an $A_{2A}$ receptor agonist. The adenosine receptor agonist may be, for instance, a small organic molecule, a protein or peptide, a nucleic acid or an antibody. In some instances, the adenosine receptor agonist is capable of substantially stimulating the endogenous activity of the adenosine receptor substantially the same as though the adenosine receptor had encountered its natural, endogenous ligand. In yet another particular embodiment, the adenosine receptor agonist, in many embodiments an adenosine $A_{2A}$ receptor agonist, is administered via an implanted device.

In one particular embodiment, an effective amount of an adenosine receptor agonist may be used in combination with one or more drugs useful in inhibiting bone resorption or inhibiting differentiation or stimulation of osteoclasts or a combination of any of these agents. Adenosine $A_{2A}$ receptor agonists are well known in the art. Many are disclosed in, for instance, U.S. Pat. Nos. 7,226,913 and 6,326,359 and in United States Patent Publication Nos. 20070225247, 20060100169, 20060034941, 20050261236, 20050182018, 20050171050, 20050020915 and 20040064039, the disclosures of which are herein incorporated by reference in their entireties. In another more particular embodiment, the adenosine $A_{2A}$ receptor agonist is selected from the group consisting of CGS 21680, MRE-0094, IB-MECA and R-PIA, binodenoson, ATL146, for instance.

The adenosine receptor agonist may be administered alone or in combination with one or more other compounds or agents for inhibiting bone resorption, osteoclast differentiation and stimulation and prosthesis loosening. Such other compounds may be, for instance, anti-inflammatory compounds, bisphosphonates or growth factors. The adenosine receptor agonist may be administered with a second adenosine receptor agonist or with a less selective adenosine receptor agonist. (i.e. one that binds other adenosine receptors in addition to $A_{2A}$, for example $A_{2B}$, $A_1$ or $A_3$).

In one embodiment, the adenosine receptor agonist may be selective for the receptor, or it may be a non-selective adenosine receptor agonist, which may stimulate or mimic natural ligands of one or more of the following receptors: $A_1$, $A_{2A}$, $A_{2B}$ or $A_3$. In a preferred embodiment, the adenosine receptor agonist is an adenosine $A_{2A}$ receptor agonist. The method may feature inhibiting osteoclast differentiation, activation or activity, or the method may further feature stimulating osteoblast differentiation, activation or activity.

In a sixth aspect, the present invention provides a pharmaceutical composition comprising an agent effective to inhibit or reduce the biological activity of an axonal guidance protein or a receptor of the axonal guidance protein, or an analog, derivative or combination thereof alone or in combination with one or more second compounds or agents effective for inhibiting bone resorption or osteoclast differentiation or stimulation. The agent effective to inhibit or reduce the biological activity of an axonal guidance protein or a receptor of the axonal guidance protein and the one or more second compounds or agents may be formulated and administered alone or together. The pharmaceutical composition(s) comprising the agent effective to inhibit or reduce the biological activity of an axonal guidance protein or a receptor of the axonal guidance protein and the one or more second compounds or agents may be administered concurrently or sequentially. In another particular embodiment, the one or more compounds or agents effective for inhibiting bone resorption or osteoclast differentiation or stimulation are selected from the group consisting of those effective for stimulating bone density and those effective for inhibiting or reducing inflammation. The pharmaceutical compositions may be delivered orally or parenterally. They may be delivered via the intravenous route, the intramuscular route, or the subcutaneous route. They may be delivered as an immediate release formulation or as a slow or sustained release formulation. In some particular embodiments, the compositions are delivered on the surface of a prosthetic device or are delivered in the very matrix of a prosthetic device.

In some embodiments, the pharmaceutical composition comprising an agent effective to inhibit or reduce the biological activity of an axonal guidance protein or a receptor of the axonal guidance protein may also contain one or more drugs selected from the group consisting of anti-inflammatory agents, growth factors, bone morphogenetic protein, soluble RANK. The axonal guidance protein may be, for instance, one of sema4D, plexin A1, and netrin-1. Also, the agent effective to inhibit or reduce the biological activity of an axonal guidance protein or a receptor of the axonal guidance protein, such as for instance netrin-1 or its receptor unc5b may be, for instance, an antibody, a peptide, a nucleic acid, for instance, an interfering RNA such as siRNA, or a small molecule.

Other objects and advantages will become apparent to those skilled in the art from a review of the following description which proceeds with reference to the following illustrative drawings.

Figure 1:
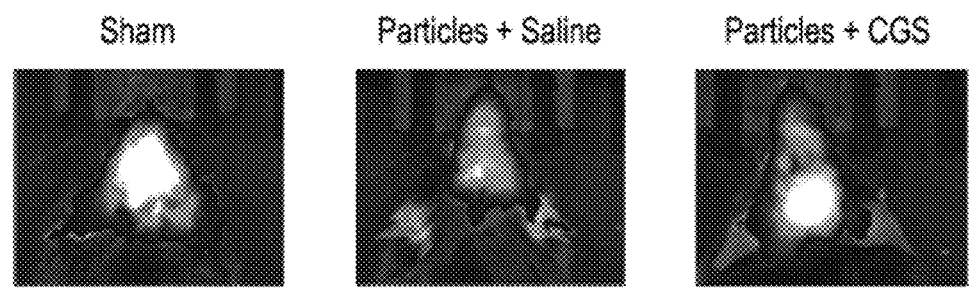
FIG. 1 demonstrates that new bone formation is reduced at sites of wear particle-induced osteolysis and is restored by adenosine $A_{2A}$ receptor stimulation. Mice (C57B1/6) underwent formation of an air pouch over the calvarium and then exposed to saline (sham) or wear particles ( ) followed by daily injections of 200 µl of saline or CGS21680, as previously described. Animals were injected with Xenolight Rediject Bone Probe 680 (2 nmoles in 150 ul) followed by scanning in the IVIS apparatus. The intensity of staining is indicated by increasing yellow coloration. The fluorescence is detectable without change for 3-4 days and persists for as long as 2 weeks although all of these scans were taken on the day of injection. Shown are representative scans of ⅕ animals per group. The intensity of fluorescence was quantitated in a specific area of interest using software provided with the apparatus and the mean (±SEM) was calculated for 5 animals in each.
Figure 1:
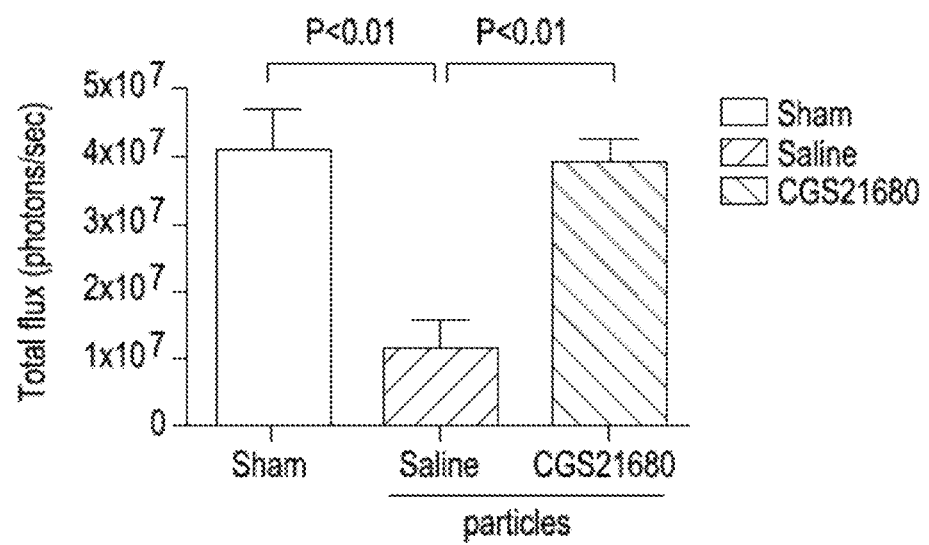

*$p<0.001$, $p<0.01$, *$p<0.5$ vs. non-stimulated control.

DETAILED DESCRIPTION OF THE INVENTION

Netrin-1 is an axonal guidance protein which acts as a chemorepulsant. Prior studies have indicated that netrin-1 is produced by activated macrophages and may play a role in the pathogenesis of atherosclerotic plaque, among other inflammatory lesions. In recent studies we have observed that netrin-1 is expressed at sites of wear particle-induced osteolysis and in other preliminary studies we have observed that netrin-1 appears to be required for osteoclast differentiation in vitro. Mice in which the bone marrow cells do not express netrin-1 (lethally irradiated mice given a bone marrow transplant with knockout marrow) have increased bone density (Dexa scan) consistent with diminished osteoclast function in vivo.

The present invention is based in part upon that discovery that it is possible to inhibit bone turnover by use of agents that either neutralize or block netrin-1 (antibodies, peptides, siRNA, etc) or agents which block its receptor (unc5b). This approach to therapy is useful for the treatment of osteoporosis, inflammatory diseases of bone, metabolic bone disease or metastatic bone disease (e.g. multiple myeloma).

Agents that block netrin-1 diminish osteoclast formation and function. Stimulation of $A_{2A}$ receptors diminishes expression of netrin-1. Consistent with the decline in RANKL-expressing cells and the decrease in RANKL in the exudate overlying osteolytic areas, $A_{2A}$ receptor stimulation diminishes osteoblast expression of RANKL by as much as 80%. Thus, $A_{2A}$ receptor agonists restore homeostasis in bone and diminish wear particle-induced osteolysis.

It appears that axonal guidance proteins and their receptors are expressed at osteolytic sites in patients and in a murine model and whether $A_{2A}$ receptors regulates their expression. The present invention features determining which cells are affected by $A_{2A}$ receptors in suppression of osteolysis and restoration of bone homeostasis. A Cre/loxP recombination system is used to selectively delete $A_{2A}$ receptors in cells of myeloid origin, osteoblasts and osteoblast precursors to determine their role in the osteolytic process and uncoupling of bone resorption and formation.

The present invention features examining the molecular mechanism by which $A_{2A}$ receptor stimulation regulates osteoblast and osteoclast function. Knockout, bone marrow chimeric and Cre/loxP recombinant mice are used with selective deletions of RANKL and axonal guidance proteins to determine whether $A_{2A}$ receptor-regulated signals play a role in the pathogenesis of osteolysis. The present invention also determines whether replacement of axonal guidance proteins reverses $A_{2A}$ receptor-mediated inhibition of osteolysis.

The present invention features dissecting intracellular signaling mechanisms by which wear particles induce and $A_{2A}$ receptor stimulation regulates expression of RANKL, sema4D, plexin A1 and netrin-1 in osteoblasts and osteoclasts. It further determines the role of wear particle phagocytosis in stimulating expression of RANKL, sema4D, plexin A1 and netrin-1 and examines signaling mechanisms at $A_{2A}$ receptors in osteoclasts and osteoblasts using pharmacologic inhibitors of signaling molecules in primary cells and cell lines and by molecular silencing techniques.

The research described herein fills two distinct knowledge gaps. First, recent studies throw new light on mechanisms of inflammatory bone resorption; inflammation uncouples bone resorption from bone generation and our recent published and preliminary studies begin to elucidate the mechanisms for inflammatory imbalance of bone generation and resorption. Second, recent work suggests a novel approach to prevention of osteolysis of bone surrounding prostheses that can be applied to diminish the need for revision arthroplasties for patients undergoing hip and knee replacement.

Results described herein will greatly expand understanding of the mechanisms underlying peri-prosthetic osteolysis and bone destruction at sites of inflammation, such as occurs in osteomyelitis and inflammatory arthritis. Moreover, based on earlier studies, novel approaches to prevention of peri-prosthetic bone loss and loosening of prosthetics will be provided. With an aging population and a growing number of younger patients undergoing total joint arthroplasty there is a critical need for methods of prolonging the life of prosthetic knees and hips to diminish the number of revision surgeries with their associated morbidities and mortality.

Every year nearly 800,000 patients undergo hip or knee replacement in the United States and it is estimated that as many as 10% of these patients will need a replacement prosthesis at a subsequent point in time. As prostheses are placed in younger patients and elderly patients remain active longer it is likely that the need for revision surgery will increase. The cost in morbidity, mortality and dollars for replacement of prostheses is high and represents a looming public health challenge. If methods can be developed that significantly prolong the half-lives of hip and knee prostheses we would predict a significant overall reduction in revision surgeries and greater longevity for those prostheses that are already in place. There is a 1%/year rate of failure of these prostheses and younger patients are at considerably greater risk of requiring revision arthroplasty (Ong, et al., *Clin Orthop Relat Res*, 2010, 468(11): 3070-6). There are greater rates of infection and subsequent loosening of revision prostheses than primary prostheses and patients, who are now older and often in worse overall health, are more likely to suffer perioperative morbidities and mortalities at the time of revision surgery as well. The results of the proposed studies will shed further light on the pathophysiology of peri-prosthetic osteolysis and will provide stronger underpinning for development of novel agents that can be used to ameliorate osteolysis, prevent premature prosthesis loosening and prolong the life of existing prostheses thereby diminishing the need for revision arthroplasty. Prolonging the life of prosthetic joints will prevent the morbidity and potential mortality of revision surgery and diminish the cost of healthcare while improving quality of life.

Netrin-1 is expressed by activated macrophages and osteoclasts and deletion of netrin-1 diminishes osteoclast differentiation in an autocrine fashion (See below). We have recently reported that stimulation of $A_{2A}$ receptors diminishes wear particle-induced osteoclast-mediated bone resorption while helping to restore bone formation (FIG. 1 and Mediero, et al., *Sci Transl Med*, 2012. 4(135): 135-65). The experiments described herein will further explore the effects of adenosine receptor stimulation on wear particle-induced osteolysis and to better understand how the effects of $A_{2A}$ receptor stimulation shed further light on the pathophysiology of osteolysis.

Adenosine $A_1$ receptors ($A_{1A}$ receptors) and $A_{2A}$ receptors regulate osteoclast differentiation both in vitro and in vivo (Kara, et al., *Arthritis Rheum*, 2010, 62(2): 534-41; Kara, et al., FASEB J, 2010, 24(7): 2325-33 and Mediero, et al., *The American Journal of Pathology*, 2012, 180(2): 775-86). $A_{1A}$ receptor blockade or deletion inhibits osteoclast formation and function in vitro (Kara, et al., *FASEB J*, 2010, 24(7): 2325-33) by enhancing ubiquitination and proteolysis of TRAF6 and disrupting the association of TAK1 with TRAF6 (Kara, et al., *FASEB J*, 2010, 24(7): 2325-33 and He, et al., *Purinergic Signal*, 2012, 8(2): 327-37). Although there is no reduction of osteoclast number in the bones of mice lacking $A_{1A}$ receptors osteoclast function in these mice is clearly diminished and bone mineral density is increased without any change in bone formation, as determined by dynamic tetracycline labeling of bone (Kara, et al., *Arthritis Rheum*, 2010, 62(2): 534-41). The disparity between in vitro and in vivo osteoclast formation is reminiscent of a similar disparity in osteoclast formation in mice lacking either TRAF6 or Atp6v0d2 in which osteoclasts are present in vivo, although functionally defective (Lomaga, et al., *Genes Dev*, 1999, 13(8): 1015-24) but do not form from precursors in vitro (Kim, N., et al., *J Exp Med*, 2005, 202(5): 589-95 and Naito, et al., *Genes Cells*, 1999, 4(6): 353-62). Moreover, $A_{2A}$ receptor stimulation inhibits osteoclast secretion of TNFα and IL-1 and osteoclast differentiation in vitro and that replacement of these cytokines restores osteoclast formation and function even in the presence of optimal concentrations of an $A_{2A}$ receptor agonist (Mediero, et al., *The American Journal of Pathology*, 2012; 180(2): 775-86), a finding that suggests that $A_{2A}$ receptor ligation diminishes osteoclast differentiation by inhibiting a cytokine-dependent amplification pathway.

Both $A_{1A}$ receptors and $A_{2A}$ receptors regulate bone metabolism when studied in vivo. Deletion or blockade of $A_{1A}$ receptors in mice leads to increased bone mineral density and prevents the loss of bone mineral density in mice after ovariectomy (Kara, et al., *Arthritis Rheum*, 2010, 62(2): 534-41). In contrast, deletion of $A_{2A}$ receptors leads to a marked decrease in bone mineral density in association with an increase in the number of osteoclasts in bone (Mediero, et al., *The American Journal of Pathology*, 2012; 180(2): 775-86). Consistent with these findings, and central to this application, application of agents that stimulate $A_{2A}$ receptors diminishes osteoclast-mediated bone resorption in a murine model of wear particle-induced osteolysis (Mediero, et al., *Sci Transl Med*, 2012; 4(135): 135-65). Human osteoclast precursors and monocytes behave in a manner consistent with that observed in mice. $A_{1A}$ receptors promote and $A_{2A}$ receptors inhibit multinucleated giant cell formation from normal human peripheral blood monocytes, a process that parallels, in many aspects, osteoclast formation (Merrill, et al., *Arth.*

*Rheum.*, 1997, 40: 1308-1315). $A_{2A}$ receptor agonists inhibit osteoclast formation by human peripheral blood monocytes (W. He and B. N. Cronstein, unpublished) and human bone marrow osteoclast precursors (Mediero, et al., *Sci Transl Med*, 2012. 4(135): 135-65).

Several recent studies reported that adenosine $A_{2B}$ receptors (A2BAR) play an important role in osteoblast differentiation and function (Gharibi, et al., *International Journal of Obesity*, 2011; Costa, et al., *Journal of Cellular Physiology*, 2011, 226(5): 1353-66; Russell, et al., *Calcif Tissue Int*, 2007, 81(4): 316-26; Evans, et al., *J Bone Miner Res*, 2006, 21(2): 228-36; and Shimegi, *Calcif Tissue Int*, 1998, 62(5): 418-25) whereas $A_{2A}$ receptors promote adipocyte differentiation from mesenchymal stem cell precursors. Moreover, cell culture studies indicate that osteoblasts produce adenosine, in large part by ecto-5' nucleotidase (CD73)-mediated dephosphorylation of AMP, which is required for osteoblast differentiation and function; in vivo deletion of CD73 leads to diminished bone density in otherwise healthy male mice (Evans, et al., *J Bone Miner Res*, 2006; 21(2): 228-36; Evans, et al., *Journal of Bone & Mineral Research*, 2006, 21(2): 228-36; Takedachi, et al., *Journal of Cellular Physiology*, 2011; Fu, et al., *Mol Cell Biol*, 2006, 26(17): 6453-68 and Tomita, et al., *Bone*, 2002, 30(1): 159-63). As in mice, stimulation of $A_{2B}$ receptors enhances human osteoblast differentiation in vitro (not shown). More interestingly, $A_{2A}$ receptor agonists suppress RANKL levels in bone of mice at sites of wear particle-induced osteolysis (Mediero, et al., *Sci Transl Med*, 2012; 4(135): 135-65) and preliminary experiments (FIG. 2) indicate that $A_{2A}$ receptor stimulation inhibits RANKL expression by osteoblasts without affecting differentiation, consistent with our published observation that treatment with an $A_{2A}$ receptor agonist diminishes RANKL concentrations in bone in the murine osteolysis model (Mediero, et al., *Sci Transl Med*, 2012. 4(135): 135-65). Interestingly $A_{2A}$ receptors are classically coupled to $G_S$ signaling mechanisms, including cAMP, which increases RANKL expression in osteoblasts (Fu, et al., *Mol Cell Biol*, 2006, 26(17): 6453-68 and Tomita, et al., *Bone*, 2002, 30(1): 159-63), the opposite of our observation. More importantly, results indicate that $A_{2A}$ receptor stimulation dampens osteolysis by multiple mechanisms and provide further support for development of $A_{2A}$ receptor agonists for the prevention of wear particle-induced bone resorption.

Adenosine receptors regulate inflammation and inflammatory cell function. Adenosine, acting at $A_2$ (subsequently identified as $A_{2A}$) receptors, inhibits inflammatory neutrophil function (Cronstein, et al., *Journal of Experimental Medicine*, 1983, 158: 1160-1177 and Cronstein, et al., *Journal of Immunology*, 1985, 135: 1366-1371) and subsequent studies demonstrate that adenosine and its receptors play a central role in the regulation of inflammatory and immune responses by monocyte/macrophages, basophils T cells and B cells (Hasko, et al., *Nat Rev Drug Discov*, 2008, 7(9): 759-70). Indeed, the anti-inflammatory effects of low-dose methotrexate, the anchor drug in therapy of Rheumatoid Arthritis, are mediated by increased adenosine concentrations in inflammatory exudates, a mechanism confirmed by others both in vitro and in patients (Chan, et al., *Nat Rev Rheumatol*, 2010, 6(3): 175-8). Osteolysis begins as an inflammatory response to wear particles that leads to activation of osteoclasts and bone destruction and the anti-inflammatory effects of adenosine, including diminished IL-1 and TNF and increased IL-10 levels in inflammatory exudates, clearly contribute to $A_{2A}$ receptor-mediated suppression of osteolysis (Mediero, et al., *Sci Transl Med*, 2012. 4(135): 135-65). In published (Mediero, et al., *Am J Pathol*, 2012, 180(2): 775-86) and preliminary studies other potentially important effects of $A_{2A}$ receptor stimulation on inflammatory cells and osteoclasts that contribute to suppression of osteolysis have been shown (see below).

Adenosine and its receptors play a critical role in the regulation of bone turnover and regeneration, and $A_{2A}$ receptor agonists diminish wear particle-induced osteolysis (Mediero, et al., *Sci Transl Med*, 2012. 4(135): 135-65). $A_{2A}$ receptor stimulation inhibits osteoclast formation and function (Mediero, et al., *The American Journal of Pathology*, 2012, 180(2): 775-86). Adenosine receptor-mediated regulation of osteoblast differentiation and function is more complex although, in general, $A_{2BA}$ receptor stimulation promotes osteoblast differentiation; interestingly $A_{2A}$ receptor stimulation inhibits osteoblast expression of RANKL without affecting differentiation. Thus, $A_{2A}$ receptor stimulation increases bone formation in mice and this effect is most likely indirect (FIG. 1).

Before the present methods and treatment methodology are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Definitions

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

By "agonist" is meant a substance that binds to a specific receptor and triggers a response in a cell. It mimics the action of an endogenous ligand (such as hormone or neurotransmitter) that binds to the same receptor. A "full agonist" binds (has affinity for) and activates a receptor, displaying full efficacy at that receptor. One example of a drug that acts as a full agonist is isoproterenol which mimics the action of acetylcholine at β adrenoreceptors. A "partial agonist" (such as buspirone, aripiprazole, buprenorphine, or norclozapine) also binds and activates a given receptor, but has only partial efficacy at the receptor relative to a full agonist. A "partial agonist" may also be considered a ligand that displays both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone. A "co-agonist" works with other co-agonists to produce the desired effect together. An antagonist blocks a receptor from activation by agonists. Receptors can be activated or inactivated either by endogenous (such as hormones and neurotransmitters) or exogenous (such as drugs) agonists and antagonists, resulting in stimulating or inhibiting a biological response. A ligand can concurrently behave as agonist and antagonist at the same receptor, depending on effector pathways.

The potency of an agonist is usually defined by its $EC_{50}$ value. This can be calculated for a given agonist by determining the concentration of agonist needed to elicit half of the maximum biological response of the agonist. Elucidating an $EC_{50}$ value is useful for comparing the potency of drugs with similar efficacies producing physiologically similar effects. The lower the $EC_{50}$, the greater the potency of the agonist and the lower the concentration of drug that is required to elicit a maximum biological response.

"Antagonist" refers to an agent that down-regulates (e.g., suppresses or inhibits) at least one bioactivity of a protein. An "antagonist" or an agent that "antagonizes" may be a compound which inhibits or decreases the interaction between a protein and another molecule, e.g., a target peptide or enzyme substrate. An antagonist may also be a compound that down-regulates expression of a gene or which reduces the amount of expressed protein present. Methods for assessing the ability of an agent to "antagonize" or "inhibit" an adenosine receptor are known to those skilled in the art.

"Analog" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention (e.g. to treat or prevent bone disease, or to modulate osteoclast differentiation), but need not necessarily comprise a compound that is similar or identical to those compounds of the preferred embodiment, or possess a structure that is similar or identical to the agents of the present invention.

"Derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

A "small molecule" refers to a molecule that has a molecular weight of less than 3 kilodaltons (kDa), preferably less than about 1.5 kilodaltons, more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is normally an organic compound (or organic compound complexed with an inorganic compound (e.g., metal)) that has a molecular weight of less than 3 kilodaltons, and preferably less than 1.5 kilodaltons, and more preferably less than about 1 kDa.

"Diagnosis" or "screening" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

The concept of "combination therapy" is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or one of the compounds may be administered first, followed by the second agent, e.g sequentially. The desired result can be either a subjective relief of one or more symptoms or an objectively identifiable improvement in the recipient of the dosage.

"Differentiate" or "differentiation" as used herein, generally refers to the process by which precursor or progenitor cells differentiate into specific cell types. In the present invention, the term refers to the process by which pre-osteoclasts become osteoclasts. Differentiated cells can be identified by their patterns of gene expression and cell surface protein expression. As used herein, the term "differentiate" refers to having a different character or function from the original type of tissues or cells. Thus, "differentiation" is the process or act of differentiating. The term "Osteoclast Differentiation" refers to the process whereby osteoclast precursors in the bone marrow become functional osteoclasts.

"Modulation" or "modulates" or "modulating" refers to up regulation (i.e., activation or stimulation), down regulation (i.e., inhibition or suppression) of a response, or the two in combination or apart. As used herein, an adenosine receptor "modulator" or "modulating" compound or agent is a compound or agent that modulates at least one biological marker or biological activity characteristic of osteoclasts and bone formation. The term "modulating" as related to osteoclast differentiation, refers to the ability of a compound or agent to exert an effect on precursors to osteoclasts, or to alter the expression of at least one gene related to osteoclastogenesis. For example, expression of the following genes is modulated during osteoclastogenesis: DC-Stamp, tartrate resistant alkaline phosphatase (TRAP), cathepsin K, calcitonin receptor, and integrin.

As used herein, the term "candidate compound" or "test compound" or "agent" or "test agent" refers to any compound or molecule that is to be tested. As used herein, the terms, which are used interchangeably, refer to biological or chemical compounds such as simple or complex organic or inorganic molecules, peptides, proteins, oligonucleotides, polynucleotides, carbohydrates, or lipoproteins. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action.

"Treatment" or "treating" refers to therapy, prevention and prophylaxis and particularly refers to administering medicine or performing medical procedures on a patient, for either prophylaxis (prevention) or to cure or reduce the extent of or likelihood of occurrence of the infirmity or malady or condition or event. In the present invention, the treatments using the agents described may be provided to slow or halt bone loss, or to increase the amount or quality of bone density. Most preferably, the treating is for the purpose of reducing or diminishing bone resorption and resultant prosthetic device loosening. Treating as used herein also means administering the compounds for increasing bone density or for modulating osteoclastogenesis in individuals. Furthermore, in treating a subject, the compounds of the invention may be administered to a subject already suffering from loss of bone mass or other bone disease as provided herein or to prevent or inhibit the occurrence of such condition.

"Subject" or "patient" refers to a mammal, preferably a human, in need of treatment for a condition, disorder or disease.

"Osteoclastogenesis" refers to osteoclast generation, which is a multi-step process that can be reproduced in vitro. Earlier in vitro osteoclastogenesis systems used mixtures of stromal or osteoblastic cells together with osteoclast precursors from bone marrow (Suda, et al., *Methods Enzymol.*, 1997, 282, 223-235; David, 1998, 13, 1730-1738). These systems utilized 1α, 25-dihydroxyvitamin $D_3$ to stimulate stromal/osteoblastic cells to produce factors that support osteoclast formation More recent models utilize bone marrow cells cultured with soluble forms of the cytokines M-CSF (macrophage-colony stimulating factor) and a soluble form of RANKL (receptor activator of nuclear factor κB ligand) (Lacey, et al., *Cell*, 1988, 93, 165-176; Shevde et al., *Proc. Natl. Acad. Sci. U.S.A.* 2000, 97, 7829-7834). These two cytokines are now recognized as the major factors from stromal cells that support osteoclastogenesis (Takahashi, et al., *Biochem. Biophys. Res. Commun.*, 1999, 256, 449-455). Thus, their addition to the culture medium overcomes the need for stromal cells.

"Osteoclast precursor" refers to a cell or cell structure, such as a pre-osteoclast, which is any cellular entity on the pathway of differentiation between a macrophage and a differentiated and functional osteoclast. The term osteoclast includes any osteoclast-like cell or cell structure which has differentiated fully or partially from a macrophage, and which has osteoclast character, including but not limited to positive staining for tartrate-resistant acid phosphatase (TRAP), but which is not a fully differentiated or functional osteoclast, including particularly aberrantly differentiated or non functional osteoclasts or pre-osteoclasts.

"Osteoclast culture" refers to any in vitro or ex vivo culture or system for the growth, differentiation and/or functional assessment of osteoclasts or osteoclast precursors, whether in the absence or presence of other cells or cell types, for instance, but not limited to, osteoblasts, macrophages, hematopoietic or stromal cells.

"Osteoclast function", as used herein, refers to bone resorption and the processes required for bone resorption.

An "amount sufficient to inhibit osteoclast differentiation, formation or function" refers to the amount of the agent sufficient to block either the differentiation, the formation or the function of osteoclasts, more particularly, an amount ranging from about 0.1 nM to about 10 µM, or more preferentially from about 0.1 nM to about 5 µM, and most preferentially from about 0.1 nM to about 1 µM in vitro. In vivo amounts of an adenosine receptor agonist such as an $A_{2A}$ receptor sufficient to block either the differentiation, the formation or the function of osteoclasts may range from about 0.1 mg/Kg of body weight per day to about 200 mg/Kg of body weight per day in vivo, or more preferentially from about 1 mg/Kg to about 100 mg/Kg, and most preferentially from about 25 mg/Kg to about 50 mg/Kg of body weight per day in vivo. It is understood that the dose, when administered in vivo, may vary depending on the clinical circumstances, such as route of administration, age, weight and clinical status of the subject in which inhibition of osteoclast differentiation, formation or function is desired.

In a specific embodiment, the term "about" means within 20%, preferably within 10%, and more preferably within 5% or even within 1%.

An "effective amount" or a "therapeutically effective amount" is an amount sufficient to decrease or prevent the symptoms associated with the conditions disclosed herein, including bone loss or in a decrease in bone mass or density, such as that which occurs with or other related conditions contemplated for therapy with the compositions of the present invention. For example, an "effective amount" for therapeutic uses is the amount of the composition comprising an active compound herein required to provide reversal or inhibition of bone loss or increase and/or accelerate bone growth, etc. Such effective amounts may be determined using routine optimization techniques and are dependent on the particular condition to be treated, the condition of the subject, the route of administration, the formulation, and the judgment of the practitioner and other factors evident to those skilled in the art. The dosage required for the compounds of the invention is that which induces a statistically significant difference in bone mass or inhibition of bone loss between treatment and control groups. This difference in bone mass or bone loss may be seen, for example, as at least 1-2%, or any clinically significant increase in bone mass or reduction in bone loss in the treatment group. Other measurements of clinically significant increases in healing may include, for example, an assay for the N-terminal propeptide of Type I collagen, tests for breaking strength and tension, breaking strength and torsion, 4-point bending, increased connectivity in bone biopsies and other biomechanical tests well known to those skilled in the art. General guidance for treatment regimens may be obtained from experiments carried out in vitro or in animal models of the disease of interest. The "effective amount" or "therapeutically effective amount" may range from about 1 mg/Kg to about 200 mg/Kg in vivo, or more preferentially from about 10 mg/Kg to about 100 mg/Kg, and most preferentially from about 25 mg/Kg to about 50 mg/Kg in vivo.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Binding compounds can also be characterized by their effect on the activity of the target molecule. Thus, a "low activity" compound has an inhibitory concentration ($IC_{50}$) (for inhibitors or antagonists) or effective concentration ($EC_{50}$) (applicable to agonists) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured.

An individual "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of a bone disease or low bone mass or density or enhanced susceptibility to bone resorption. An individual having one or more of these risk factors has a higher probability of developing bone resorption than an individual without these risk factors.

"Prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

General Description

The invention relates to the unexpected finding that agents that inhibit or reduce the activity of an axonal guidance protein, such as netrin-1, or that bind to or block a receptor for the same, including for instance, adenosine $A_{2A}$ receptor agonists, lead to or result in inhibition of osteoclast differentiation, formation, or function, leads to less bone resorption, and subsequently increased bone density and osteoblast stimulation or activation or differentiation. As such, these agents may be used to treat a subject having a condition characterized by bone loss.

Selecting the compounds that interact with or bind to a protein, peptide or receptor or otherwise antagonize or agonize or stimulate the receptor may be performed in multiple ways. The compounds may first be chosen based on their structural and functional characteristics, using one of a number of approaches known in the art. For instance, homology modeling can be used to screen small molecule libraries in order to determine which molecules are candidates to interact with the receptor thereby selecting plausible targets. The compounds to be screened can include both natural and synthetic ligands. Furthermore, any desired compound may be examined for its ability to interact with or bind to the receptor.

Binding to or interaction with an axonal guidance protein or a receptor for the same may be determined by performing an assay such as, for example, a binding assay between a desired compound and a receptor. In one aspect, this is done by contacting said compound to a protein, peptide or receptor and determining its dissociation rate. Numerous possibilities for performing binding assays are well known in the art. The indication of a compound's ability to bind to a protein, peptide or receptor is determined, e.g., by a dissociation rate, and the correlation of binding activity and dissociation rates is well established in the art. For example, the assay may be performed by radio-labeling a reference compound, or other suitable radioactive marker, and incubating it with the cell bearing a receptor. Test compounds are then added to these reactions in increasing concentrations. After optimal incubation, the reference compound and receptor complexes are separated, e.g., with chromatography columns, and evaluated for bound $^{125}$I-labeled peptide with a gamma ($\gamma$) counter. The amount of the test compound necessary to inhibit 50% of the reference compound's binding is determined. These values are then normalized to the concentration of unlabeled reference compound's binding (relative inhibitory concentration $(RIC)^{-1}$=concentration$_{test}$/concentration$_{reference}$). A small $RIC^{-1}$ value indicates strong relative binding, whereas a large $RIC^{-1}$ value indicates weak relative binding. See, for example, Latek et al., Proc. Natl. Acad. Sci. USA, 2000, 97(21): 11460-11465. A receptor agonist mimic may be computationally evaluated and designed by means of a series of steps in which chemical groups or fragments are screened and selected for their ability to associate with the individual binding pockets or interface surfaces of the protein. One skilled in the art may employ one of several methods to screen chemical groups or fragments for their ability to associate with the receptor. This process may begin by visual inspection of, for example, the protein/protein interfaces or the binding site on a computer screen based on the available crystal complex coordinates of the receptor, including a protein known to interact with selected fragments or chemical groups may then be positioned in a variety of orientations, or docked, at an individual surface of the receptor that participates in a protein/protein interface or in the binding pocket. Docking may be accomplished using software such as QUANTA and SYBYL, followed by energy minimization and molecular dynamics with standard molecular mechanics forcefields, such as CHARMM and AMBER (AMBER, version 4.0 (Kollman, University of California at San Francisco, copyright, 1994); QUANTA/CHARMM (Molecular Simulations, Inc., Burlington, Mass., copyright, 1994)). Specialized computer programs may also assist in the process of selecting fragments or chemical groups. These include: GRID (Goodford, *J. Med. Chem.*, 1985, 28:849-857), available from Oxford University, Oxford, UK; MCSS (Miranker, et al., *Proteins: Structure, Function and Genetics,* 1991, 11:29-34), available from Molecular Simulations, Burlington, Mass.; AUTODOCK (Goodsell, et al., *Proteins: Structure, Function, and Genetics,* 1990, 8:195-202), available from Scripps Research Institute, La Jolla, Calif.; and DOCK (Kuntz et al., *J. Mol. Biol.,* 1982, 161:269-288), available from University of California, San Francisco, Calif. Once suitable chemical groups or fragments that bind to an adenosine receptor have been selected, they can be assembled into a single compound or agonist. Assembly may proceed by visual inspection of the relationship of the fragments to each other in the three-dimensional image displayed on a computer screen in relation to the structure coordinates thereof. This would be followed by manual model building using software such as QUANTA or SYBYL. Useful programs to aid one of skill in the art in connecting the individual chemical groups or fragments include: CAVEAT (Bartlett et al., 1989, 'CAVEAT: A Program to Facilitate the Structure-Derived Design of Biologically Active Molecules'. In Molecular Recognition in Chemical and Biological Problems', Special Pub., Royal Chem. Soc. 78:182-196), available from the University of California, Berkeley, Calif.; 3D Database systems such as MACCS-3D (MDL Information Systems, San Leandro, Calif.). This area is reviewed in Martin, *J. Med. Chem.,* 1992, 35:2145-2154); and HOOK (available from Molecular Simulations, Burlington, Mass.). Instead of proceeding to build an adenosine receptor agonist mimic, in a step-wise fashion one fragment or chemical group at a time, as described above, such compounds may be designed as a whole or 'de novo' using either an empty binding site or the surface of a protein that participates in protein/protein interactions or optionally including some portion(s) of a known activator(s). These methods include: LUDI (Bohm, *J. Comp. Aid. Molec. Design* 1992, 6:61-78), available from Molecular Simulations, Inc., San Diego, Calif.; LEGEND (Nishibata et al., *Tetrahedron,* 1991, 47:8985), available from Molecular Simulations, Burlington, Mass.; and LeapFrog (available from Tripos, Inc., St. Louis, Mo.). Other molecular modeling techniques may also be employed in accordance with this invention. See, e.g., Cohen et al., *J. Med. Chem.,* 1990, 33:883-894. See also, Navia, et al., *Current Opinions in Structural Biology,* 1992, 2:202-210.

Once a compound has been designed by the above methods, the efficiency with which that compound may bind to or interact with the receptor protein may be tested and optimized by computational evaluation. Agonists may interact with the receptor in more than one conformation that is similar in overall binding energy. In those cases, the deformation energy of binding is taken to be the difference between the energy of the free compound and the average energy of the conformations observed when the inhibitor binds to the receptor protein.

A compound selected for binding to the receptor may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the compound and the receptor protein when the mimic is bound to it preferably make a neutral or favorable contribution to the enthalpy of binding. Specific computer software is available in the art to evaluate compound deformation energy and electrostatic interaction. Examples of programs designed for such uses include: Gaussian 92, revision C (Frisch, Gaussian, Inc., Pittsburgh, Pa. copyright 1992); AMBER, version 4.0 (Kollman, University of California at San Francisco, copyright 1994); QUANTA/CHARMM (Molecular Simulations, Inc., Burlington, Mass., copyright 1994); and Insight II/Discover (Biosym Technologies Inc., San Diego, Calif., copyright 1994). These programs may be implemented, for instance, using a computer workstation, as are well-known in the art. Other hardware systems and software packages will be known to those skilled in the art.

Once a receptor modulating compound has been optimally designed, for example as described above, substitutions may then be made in some of its atoms or chemical groups in order to improve or modify its binding properties, or its pharmaceutical properties such as stability or toxicity. Generally, initial substitutions are conservative, i.e., the replacement group will have approximately the same size, shape, hydrophobicity and charge as the original group. Substitutions known in the art to alter conformation should be avoided. Such altered chemical compounds may then be analyzed for efficiency of binding to the receptor by the same computer methods described in detail above.

Candidate Compounds and Agents

Examples of agents, candidate compounds or test compounds include, but are not limited to, nucleic acids (e.g., DNA and RNA), carbohydrates, lipids, proteins, peptides, peptidomimetics, small molecules and other drugs. In one preferred aspect, agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, *Anticancer Drug Des.,* 1997, 12:145; U.S. Pat. No. 5,738,996 and U.S. Pat. No. 5,807,683).

Phage display libraries may be used to screen potential ligands or adenosine receptor modulators. Their usefulness lies in the ability to screen, for example, a library displaying a large number of different compounds. For use of phage display libraries in a screening process, see, for instance, Kay, et al., *Methods,* 2001, 240-246. An exemplary scheme for using phage display libraries to identify compounds that bind or interact with an adenosine receptor may be described as follows: initially, an aliquot of the library is introduced into microtiter plate wells that have previously been coated with target protein, e.g. $A_{2A}$ receptor. After incubation (e.g., 2 hours), the nonbinding phage are washed away, and the bound phage are recovered by denaturing or destroying the target with exposure to harsh conditions such as, for instance pH 2, but leaving the phage intact. After transferring the phage to another tube, the conditions are neutralized, followed by infection of bacteria with the phage and production of more phage particles. The amplified phage are then rescreened to complete one cycle of affinity selection. After three or more rounds of screening, the phage are plated out such that there are individual plaques that can be further analyzed. For example, the conformation of binding activity of affinity-purified phage for the adenosine $A_{2A}$ receptor may be obtained by performing ELISAs. One skilled in the art can easily perform these experiments. In one aspect, an $A_{2A}$ receptor molecule used for any of the assays may be a recombinant $A_{2A}$ receptor protein, or an $A_{2A}$ fusion protein, an analog, derivative, or mimic thereof.

Examples of methods for the synthesis of molecular libraries can be found in the art, for example in: DeWitt et al., *Proc. Natl. Acad. Sci. USA,* 1993, 90:6909; Erb et al., *Proc. Natl. Acad. Sci. USA,* 1994, 91:11422; Zuckermann et al., *J. Med. Chem.,* 1994, 37:2678; Cho et al., *Science,* 1993, 261:1303; Carrell et al., *Angew. Chem. Int. Ed. Engl.,* 1994, 33:2059; Carell et al., *Angew. Chem. Int. Ed. Engl.,* 1994, 33:2061; and Gallop et al., *J. Med. Chem.,* 1994, 37:1233.

Libraries of compounds may be presented, e.g., in solution (Houghten, *Bio/Techniques,* 1992, 13:412-421), or on beads (Lam, *Nature,* 1991, 354:82-84), chips (Fodor, *Nature,* 1993, 364:555-556), bacteria (U.S. Pat. No. 5,223,409), spores (U.S. Pat. Nos. 5,571,698; 5,403,484; and 5,223,409), plasmids (Cull et al., *Proc. Natl. Acad. Sci. USA* 1992, 89:1865-1869) or phage (Scott, et al., *Science,* 1990, 249:386-390; Devlin, *Science,* 1990, 249:404-406; Cwirla et al., *Proc. Natl. Acad. Sci. USA,* 1990, 87:6378-6382; and Felici, *J. Mol. Biol.,* 1991, 222:301-310).

The methods of screening compounds may also include the specific identification or characterization of such compounds, whose effect on bone resorption was determined by the methods described above. If the identity of the compound is known from the start of the experiment, no additional assays are needed to determine its identity. However, if the screening for compounds that modulate the protein, peptide or receptor is done with a library of compounds, it may be necessary to perform additional tests to positively identify a compound that satisfies all required conditions of the screening process. There are multiple ways to determine the identity of the compound. One process involves mass spectrometry, for which various methods are available and known to the skilled artisan (e.g. the neogenesis website). Neogenesis' ALIS (automated ligand identification system) spectral search engine and data analysis software allow for a highly specific identification of a ligand structure based on the exact mass of the ligand. One skilled in the art can also readily perform mass spectrometry experiments to determine the identity of the compound.

Antibodies, including polyclonal and monoclonal antibodies, for instance anti-$A_{2A}$ receptor antibodies and neutralizing antibodies may be useful as compounds to modulate osteoclast differentiation and/or function. These antibodies are available from such vendors as Upstate Biologicals, Santa Cruz, or they made be prepared using standard procedures for preparation of polyclonal or monoclonal antibodies known to those skilled in the art. Also, antibodies including both polyclonal and monoclonal antibodies, and drugs that modulate the activity of the adenosine receptor and/or its subunits may possess certain diagnostic applications and may for example, be utilized for the purpose of detecting and/or measuring conditions such as bone diseases, bone loss, or osteoclast differentiation and/or function. The adenosine receptor or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or act as agonists for the activities of the $A_{2A}$ receptor may be discovered or synthesized, and may be used in diagnostic and/or therapeutic protocols.

Therapeutic and Prophylactic Compositions and their Use

Candidates for therapy with the agents identified by the methods described herein are patients either suffering from bone resorption or at risk for doing so.

The invention provides methods of treatment featuring administering to a subject an effective amount of an agent of the invention. The compound is preferably substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject. Accordingly, the agents identified by the methods described herein may be formulated as pharmaceutical compositions to be used for prophylaxis or therapeutic use to treat these patients.

Various delivery systems are known and can be used to administer a compound of the invention, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the compound can be delivered in a vesicle, in particular a liposome (Langer, *Science,* 1990, 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327)

In yet another embodiment, the compound can be delivered in a controlled or sustained release system. In one embodiment, a pump may be used (see Langer, supra; Sefton *CRC Crit. Ref Biomed. Eng.* 1987, 14:201; Buchwald et al., *Surgery,* 1980, 88:507; Saudek et al., *N Engl. J. Med.* 1989, 321:574). In another embodiment, polymeric materials can be used (See, Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., *Macromol. Sci. Rev. Macromol. Chem.* 1983, 23:61; Levy et al., *Science,* 1985, 228:190; During et al. *Ann. Neurol.,* 1989, 25:351; Howard et al., *J. Neurosurg.,* 1989, 71:105). In yet another embodiment, a controlled release system can be placed in proximity of the therapeutic target, i.e., the subject bone or prosthesis, thus requiring only a fraction of the systemic dose (see, e.g., Goodson, in Medical Applications of Controlled Release (1984) supra, vol. 2, pp. 115-138). Other suitable controlled release systems are discussed in the review by Langer, *Science,* 1990, 249:1527-1533.

The present invention further contemplates therapeutic compositions useful in practicing the therapeutic methods of this invention. A subject therapeutic composition includes, in admixture, a pharmaceutically acceptable excipient (carrier) and one or more of an adenosine receptor modulator, such as an adenosine $A_{2A}$ receptor agonist, as described herein as an active ingredient. In a preferred embodiment, the composition comprises one or more compounds or agents capable of mimicking or serving as an agonist for the adenosine $A_{2A}$ receptor.

Effects of the compounds or agents of the invention can first be tested for their ability to stimulate or mimic the adenosine receptor using standard techniques known in the art. More particularly, the selectivity of the compounds for the receptor can be assessed using radioligand binding assays whereby a test or candidate compound can be assayed for its ability to bind to a cell having or expressing the receptor (including any of the known adenosine receptors, $A_1$, $A_{2A}$, $A_{2B}$ or $A_3$). Cells can be transfected with the nucleic acid encoding the various adenosine receptors and competitive binding assays with radiolabeled ligands run to evaluate the specificity of the particular candidate compounds. The cDNAs for human $A_1$ (see GenBank accession number BCO26340), $A_{2A}$ (see GenBank accession number $NM_{000675}$), $A_{2B}$ (see GenBank accession number $NM_{000676}$) or $A_3$ (see GenBank accession number AY136749 or L22607 or $NM_{000677}$) can be used to prepare the nucleic acid constructs for use in these methods.

The present compounds or agents that modulate the axonal guidance protein or its receptor or an adenosine receptor themselves can be used as the sole active agents, or can be used in combination with one or more other active ingredients. In particular, combination therapy using the adenosine receptor agonists with one or more other agents is contemplated. These agents are known in the art, and can be selected from anti-inflammatory compounds, bisophosphonates, soluble RANK, and bone morphogenetic proteins, for instance.

When contemplating combination therapy with an adenosine receptor agonist and one or more of the above-noted agents, it is important to assess clinical safety by methods known to those skilled in the art. Appropriate dose titration may be necessary when certain groups of compounds are contemplated for use together.

The compounds or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Preferably, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treating it with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the preferred embodiment, the matrix is biodegradable over a time period of less than a year, more preferably less than six months, most preferably over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). A hydrogel is defined as a substance formed when an organic polymer (natural or synthetic) is cross-linked via covalent, ionic, or hydrogen bonds to create a three-dimensional open-lattice structure which entraps water molecules to form a gel. In general, these polymers are at least partially soluble in aqueous solutions, such as water, buffered salt solutions, or aqueous alcohol solutions, that have charged side groups, or a monovalent ionic salt thereof.

For use in treating animal subjects, the compositions of the invention can be formulated as pharmaceutical or veterinary compositions. Depending on the subject to be treated, the mode of administration, and the type of treatment desired, e.g., prevention, prophylaxis, therapy; the compositions are formulated in ways consonant with these parameters. A summary of such techniques is found in Remington's Pharmaceutical Sciences, latest edition, Mack Publishing Co., Easton, Pa.

The preparation of therapeutic compositions containing small organic molecules polypeptides, analogs or active fragments as active ingredients is well understood in the art. The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Formulations may be prepared in a manner suitable for systemic administration or for topical or local administration. Systemic formulations include, but are not limited to those designed for injection (e.g., intramuscular, intravenous or subcutaneous injection) or may be prepared for transdermal, transmucosal, nasal, or oral administration. Such compositions may be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. The formulation will generally include a diluent as well as, in some cases, adjuvants, buffers, preservatives and the like. In addition, if desired, the composition can contain minor amounts of auxiliary substances such as wetting or emulsifying agents, pH buffering agents which enhance the effectiveness of the active ingredient.

A small organic molecule/compound, a polypeptide, an analog or active fragment thereof can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. For oral administration, the compositions can be administered also in liposomal compositions or as microemulsions. Suitable forms include syrups, capsules, tablets, as is understood in the art.

The compositions of the present invention may also be administered locally to sites in subjects, both human and other vertebrates, such as domestic animals, rodents and livestock, using a variety of techniques known to those skilled in the art. For example, these may include sprays, lotions, gels or other vehicles such as alcohols, polyglycols, esters, oils and silicones.

The administration of the compositions of the present invention may be pharmacokinetically and pharmacodynamically controlled by calibrating various parameters of administration, including the frequency, dosage, duration mode and route of administration. Variations in the dosage, duration and mode of administration may also be manipulated to produce the activity required.

The therapeutic compositions are conventionally administered in the form of a unit dose, for instance intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the agent selected for treating the subject, the dosage formulation, and in a therapeutically effective amount. If one desires to achieve the desired effect in vitro, the effective amounts may range from about 0.1 nM to about 10 nM, more preferably about 0.1 nM to about 5 nM, and most preferably from about 0.1 nM to about 1 nM. The desired effect refers to the effect of the agent on reducing or inhibiting osteoclast differentiation or stimulation, reducing or inhibiting bone resorption and reducing or inhibiting loosening of a medical prosthesis. Moreover, the quantity of the adenosine receptor agonist to be administered depends on the subject to be treated, and degree of stimulation or mimicry of the adenosine receptor desired or the extent or severity of bone resorption. Precise amounts of active ingredient required to be administered depend on the judgment of the practitioner and are peculiar to each individual. However, suitable dosages to achieve the desired therapeutic effect in vivo may range from about 0.1 mg/kg body weight per day to about 200 mg/kg body weight per day, or from about 1.0 mg/kg body weight per day to about 100 mg/kg body weight per day, preferably about 25 mg/kg body weight per day to about 50 mg/kg body weight per day. In a particular embodiment, the term "about" means within 20%, preferably within 10%, and more preferably within 5%. The preferred dose will depend on the route of administration. However, dosage levels are highly dependent on the nature of the disease or situation, the condition of the subject, the judgment of the practitioner, and the frequency and mode of administration. If the oral route is employed, the absorption of the substance will be a factor effecting bioavailability. A low absorption will have the effect that in the gastro-intestinal tract higher concentrations, and thus higher dosages, will be necessary. Suitable regimes for initial administration and further administration are also variable, but are typified by an initial administration followed by repeated doses at one or more hour intervals by a subsequent injection or other administration. Alternatively, continuous intravenous infusion sufficient to maintain desired concentrations, e.g. in the blood, are contemplated. The composition may be administered as a single dose multiple doses or over an established period of time in an infusion.

It will be understood that the appropriate dosage of the substance should suitably be assessed by performing animal model tests, where the effective dose level (e.g., $ED_{50}$) and the toxic dose level (e.g. $TD_{50}$) as well as the lethal dose level (e.g. $LD_{50}$ or $LD_{10}$) are established in suitable and acceptable animal models. Further, if a substance has proven efficient in such animal tests, controlled clinical trials should be performed.

The compounds or compositions of the present invention may be modified or formulated for administration at the site of pathology. Such modification may include, for instance, formulation which facilitate or prolong the half-life of the compound or composition, particularly in the environment. Additionally, such modification may include the formulation of a compound or composition to include a targeting protein or sequence which facilitates or enhances the uptake of the compound/composition to bone or bone precursor cells. In a particular embodiment, such modification results in the preferential targeting of the compound to bone or bone precursor cells versus other locations or cells. In one embodiment, a tetracycline, tetracycline family or bisphosphonate may be utilized to target the compound or composition of the present invention to bone or bone cells, including osteoclasts and osteoclast precursors. Novel heterocycles as bone targeting compounds are disclosed in U.S. Patent Publication No. 2002/0103161 $A_1$, which is incorporated herein by reference in its entirety.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Sterile injectable forms of the compositions may be aqueous or oleaginous suspensions. The suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis.

The pharmaceutical compositions may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The invention also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Effective Doses

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to unaffected cells and, thereby, reduce side effects.

The data obtained from cell culture assays and animal studies can be used in formulating a dose range for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to optimize efficacious doses for administration to humans. Plasma levels can be measured by any technique known in the art, for example, by high performance liquid chromatography.

In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Normal dose ranges used for particular therapeutic agents employed for specific diseases can be found in the Physicians' Desk Reference 54th Edition (2000).

EXAMPLES

The following examples are set forth to provide those of ordinary skill in the art with a description of how to make and use the methods and compositions of the invention, and are not intended to limit the scope thereof. Efforts have been made to insure accuracy of numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Identifying Molecules that Regulate Osteoclast-Osteoblast Interactions at Sites of Osteolysis and Determine the Effect of $A_{2A}$ R Stimulation on Expression of these Molecules Wear particles induce inflammatory changes that directly uncouple bone resorption and generation. Among the factors that uncouple bone resorption and generation are cytokines, Wnt-Frizzled antagonists and axonal guidance molecules. $A_{2A}$ R stimulation diminishes osteolysis and regulates expression of factors that uncouple bone resorption and regeneration.

Background $A_{2A}$ receptor stimulation diminishes osteolysis in a well-established murine model of wear particle-induced bone resorption (Mediero, et al., *Sci Transl Med*, 2012. 4(135): 135-65). In this model ultra high molecular weight polyethylene particles (UHMWPE) are injected into an air pouch overlying the calvaria and the area of bone resorption is measured. This is a convenient model as the soluble factors released by the tissue are available for sampling after in vitro culture of tissues and the changes in the levels of these agents offer important insights, along with the histologic and immunohistologic analysis of the affected bone, into the pathophysiology of wear particle-induced bone resorption. As expected, a marked increase in the number of osteoclasts in the affected bone (cells positive for Cathepsin K, RANK, osteopontin) as well as increased production of stimuli for osteoclast differentiation (M-CSF, RANK, IL-1 and TNFα) was observed. Although there was no change in the number of osteoblasts expressing osteocalcin in the calvariae, there was a marked increase in the number of RANKL+ cells with a reciprocal decrease in osteoprotegerin+ cells, an observation that suggests direct effects of wear particle-induced inflammation on expression of RANKL and osteoprotegerin in stromal cells or osteoblasts. The bulk of the infiltrating inflammatory cells were CD68+ and appeared to be monocytes. Bone resorption may be inhibited or halted and nearly all of these changes may be reversed by treatment with an $A_{2A}$ receptor agonist. The $A_{2A}$ receptor agonist completely reversed the wear particle-induced increase in osteoclasts, macrophages and other inflammatory cells while reducing the number of RANKL-expressing cells and normalizing the number of osteoprotegerin+ cells. In preliminary studies it was observed that the inflammatory infiltrate in mice and, to a lesser extent, humans, composed primarily of macrophages, expresses high levels of sema4D (FIG. 3), a protein known to turn off osteoblast bone production both in vitro and in vivo (Negishi-Koga, et al., *Nat Med*, 2011, 17(11): 1473-80), an observation that suggests a complementary mechanism for uncoupling bone generation and resorption. Treatment with the $A_{2A}$ receptor agonist CGS21680 dramatically decreased the number of sema4D-expressing cells in the calvaria. Surprisingly, the infiltrating macrophages and the osteoclasts also appeared to express high levels of netrin-1 (FIG. 4), an axonal guidance protein previously implicated in stimulating macrophage function to promote plaque persistence in atherosclerosis (van Gils, et al., *Nat Immunol*, 2012, 13(2): 136-43).

Netrin-1 was shown to play a role in osteoclast formation since bone marrow-derived osteoclast precursors from netrin-1$^{-/-}$ bone marrow chimeric mice do not form osteoclasts in vitro in response to RANKL and M-CSF, an effect reversed by exogenous netrin-1 (FIG. 4). Moreover, $A_{2A}$ receptor-mediated inhibition of osteoclast differentiation is also reversed by exogenous netrin-1 indicating that inhibition of netrin-1 expression is critical for $A_{2A}$ receptor-mediated inhibition of osteoclast differentiation. Consistent with this observation it was shown that radiation chimeras with netrin-1$^{-/-}$ replacement bone marrow have increased bone mineral density, as measured by Dexa scan (FIG. 4). Finally, it was shown that expression of sema3A, plexin A1, neuropilin-1, ephB3 and ephrin B3 expression were unaffected in the calvarial tissue of $A_{2A}$ receptor agonist-treated mice although $A_{2A}$ receptor stimulation increases cultured osteoblast expression of sema3A and osteoclast expression of plexin A1 (mRNA and protein), the co-receptor for sema3A (Not shown). Thus, these results indicate that there are potentially multiple complementary pathways by which wear particle-induced inflammation promotes bone resorption in addition to those currently recognized. The relevance of these observations is underscored by the finding in preliminary studies that sema4D- and netrin-1-expressing cells are present in tissue obtained from patients undergoing prosthesis revision due to osteolysis (FIGS. 3 and 4).

Materials and Methods.

Immunohistochemical staining of decalcified, paraffin-embedded sections of either experimental osteolysis will be used as we have recently described (Mediero, et al., *Sci Transl Med*, 2012. 4(135): 135-65) or of material from patients undergoing revision of prostheses to determine whether specific molecules are expressed and, if so, on which cells. This approach was previously used to demonstrate that an $A_{2A}$ R agonist could diminish the number of osteoclasts and increase the apparent number of osteoblasts at sites of wear particle-induced osteolysis. Paraffin embedded tissue sections already generated in the murine model (previously described in (Mediero, et al., *Sci Transl Med*, 2012. 4(135): 135-65) will be used, using antibodies that decorate the molecules of interest in fixed, paraffin-embedded tissue as shown in preliminary studies. In addition, similar studies on tissue sections from patients who have undergone revision of prostheses will be performed, using sections from material from patients that have recently been reported Vasudevan, et al., *Arthritis Rheum*, 2012, 64(4): 1005-14). In preliminary experiments the change in expression of axonal guidance proteins from unstimulated osteoclast precursors to osteoclasts were observed using a specially designed microarray that demonstrated that message for a number of axonal guidance proteins were regulated (>1.5-fold change) in osteoclasts as compared to osteoclast precursors (Data not shown). Using these results and the results of previous studies as a guide, probes will be performed, using immunohistochemical methods, for expression of: semaphorins 4D, 3A and 7; netrin-1 and its receptor UNC5b; the neurotrophins nerve growth factor (NGF), brain-derived neurotrophic factor (BDNF) and neurotrophin-3 and their receptors TrkA, B and C.

Results.

As shown in FIG. 3 there is a marked increase in the number of sema4D expressing cells that, for the most part, colocalize with CD68+ macrophages in the inflammatory infiltrate of mice exposed to wear particles (CD68 staining was previously reported in (Mediero, et al., *Sci Transl Med*, 2012. 4(135): 135-65). Application of an $A_{2A}$ receptor agonist dramatically reduces the inflammatory infiltrate and number of cells expressing sema4D. The multinucleated cells in close apposition to bone (presumably osteoclasts) also lose expression of sema4D in the $A_{2A}$ agonist-treated mice and, when studied in vitro, $A_{2A}$ receptor ligation inhibits expression of sema4D mRNA by murine osteoclasts and the murine RAW264.7 murine cell line induced to undergo osteoclast differentiation (FIG. 3). Dramatic changes for some, but not all, other determinants will be observed. Although these results are qualitative the goal of this aim is to focus the subsequent aims so that only those determinants that are dramatically affected will be studied for their role in osteolysis and as targets for $A_{2A}$ receptor agonists. Correlation between the presence/absence of specific markers in tissue from mice and patients with osteolysis undergoing revision of their prostheses will further support subsequent experiments in this area. Only those axonal guidance proteins and neurotrophins for which differences between control and wear particle-treated mice and mice treated with an $A_{2A}$ receptor agonist are observed will be analyzed. It will be determined whether there is any correlation between expression of these molecules in tissues from patients undergoing prosthesis revision due to osteolysis.

Murine modeling suggests that events taking place in the inflammatory infiltrate play a major role in promoting bone destruction. Moreover, the most striking effect of $A_{2A}$ receptor stimulation in the murine model of osteolysis is almost complete reduction of the inflammatory infiltrate despite the presence of the wear particles. Thus, if the immunohistological analysis of the changes in the inflammatory infiltrate in patients is paralleled in the murine model that resulting changes in the bone in mice exposed to wear particles will be paralleled in the bone of patients undergoing prosthesis revision due to osteolysis.

Staining for netrin-1 was carried out in collaboration with Dr. Kathryn Moore's laboratory, an internationally known expert on the role of this protein in macrophage function in atherosclerosis (van Gils, et al., *Nat Immunol*, 2012, 13(2): 136-43). In those cases where it is indicated immunohistology with fluorescent antibodies will be used to better define the cells expressing the molecules of interest, as with netrin-1.

Example 2

Determine which Cells are Affected by $A_{2A}$ Rs in Suppression of Osteolysis and Restoration of Bone Homeostasis Osteoclasts and osteoblasts regulate each other's function during wear particle-induced osteolysis and $A_{2A}$ receptor stimulation regulates expression of intercellular signals to restore bone homeostasis.

Background

Osteoclasts and osteoblasts form a tight unit in regulation of bone formation and destruction. Some notable examples of the interdependence of osteoblasts and osteoclasts include osteoblasts stimulate osteoclast differentiation via expression of both surface and soluble RANKL and inhibit osteoclast differentiation via secretion of osteoprotegerin (a decoy) and sema3A (which binds to plexin A1 on osteoclasts); osteoclasts secrete sema4D which inhibits osteoblast differentiation. At inflamed sites other factors, produced by inflammatory cells, also likely play a role in regulating bone metabolism, e.g. TNF osteoclast differentiation and function and DKK inhibits osteoblast differentiation and function Walsh, et al., *Immunol Rev*, 2010, 233(1):301-12). $A_{2A}$ receptor stimulation decreases RANKL, TNFα and IL-1 and increases osteoprotegerin and IL-10 production by bone at sites of osteolysis in a murine model (Mediero, et al., *Sci Transl Med*, 2012. 4(135): 135-65). As noted above, $A_{2A}$ receptor stimulation diminishes osteoblast production of RANKL, and previous work has demonstrated that $A_{2A}$ receptors inhibit production of TNF and IL-1 and increase IL-10 secretion by macrophages (Reviewed in (Hasko, et al., *Nat Rev Drug Discov*, 2008, 7(9): 759-70)). As has been previously demonstrated (Mediero, et al., *Sci Transl Med*, 2012; 4(135): 135-65), $A_{2A}$ receptors diminish wear particle-induced osteolysis although the cell(s) responsible for this change have not been fully established. Because there are $A_{2A}$ receptor-mediated effects on all of the cell types that may contribute to inhibition of osteolysis the effect of selective $A_{2A}$ receptor knockdown on wear particle-induced osteolysis will be tested in a murine model taking advantage of conditional $A_{2A}$ receptor knockout mice.

Materials and Methods.

Selective deletion of $A_{2A}$ receptor in cells of myeloid origin (including neutrophils, monocytes and macrophages), osteoclasts and osteoblasts and other cell types (B cells) will be used to determine which cells are regulated by the $A_{2A}$ receptor agonist CGS21680 in suppressing osteolysis. Targeting a gene deletion to a specific tissue or cell type of interest using the Cre/loxP recombination system can circumvent many limitations of global gene knockout models and specifically identify cells involved in pathogenesis. In collaboration with Joel Linden, a colleague at La Jolla Institute for Allergy and Immunology, we will study the effect of selective $A_{2A}$ receptor deletion using $A_{2a}$(flox/flox) mice (C57B1/6 background) provided by Dr. Linden (Reutershan, et al., *Journal of Immunology*, 2007, 179(2): 1254-63). In addition to providing the $A_{2a}$(flox/flox) mice he will provide us with $A_{2a}$(flox/flox)×Lck-cre and $A_{2a}$(flox/flox)×CD19-cre mice with selective deletion of $A_{2A}$ receptors in myeloid cells and B cells (all strains on C57B1/6 background), respectively. To more precisely target $A_{2A}$ receptor deletion we will generate $A_{2a}$(flox/flox)×TRAP-cre and $A_{2a}$(flox/flox)×Col 2.3-cre mice in which the $A_{2A}$ receptor knockout is selectively targeted to osteoclasts (Chiu, et al., *Genesis*, 2004, 39(3): 178-85) and osteoblasts (Liu, et al., Int *J Dev Biol*, 2004, 48(7): 645-53), respectively. The TRAP-cre mice are commercially available from Jackson Laboratories for use in breeding and our co-PI Dr. Partridge of the NYU College of Dentistry will provide Col 2.3-cre mice for breeding purposes. Because plasma cells and B cells have formed a prominent part of the inflammatory infiltrate at sites of osteolysis in patients with Rheumatoid Arthritis undergoing prosthesis revision (Vasudevan, et al., *Arthritis Rheum*, 2012, 64(4): 1005-14) we will also study the effect of $A_{2A}$ receptor stimulation on osteolysis in $A_{2a}$ (flox/flox)×CD19-cre, in which $A_{2A}$ receptors are selectively deleted in B cells.

In these experiments osteolysis will be monitored as porosity of the calvaria, measured by microCT, as has been previously described (Mediero, et al., *Sci Transl Med*, 2012. 4(135): 135-65). The effect of selective $A_{2A}$ receptor deletion on treated and control histologic and immunohistologic changes in the affected bone will be determined Thus, the expression of RANK and RANKL, TRAP and cathepsin K, osteoprotegerin, CD68 (macrophages), TNFα, osteopontin, osteocalcin, sema4D, sema3A, netrin-1, plexins A1 and B1, and other neurotrophins, will be examined (Mediero, et al., *Sci Transl Med*, 2012. 4(135): 135-65). In addition, sema4D, netrin-1, GM-CSF, M-CSF, IP-10, MCP-1, IL-1, TNF, IL-6, IL-10, osteoprotegerin, osteocalcin and RANKL in supernates of cultured calvaria will be quantified by luminex assay, as has been previously described (Mediero, et al., *Sci Transl Med*, 2012. 4(135): 135-65). Finally, the effect of the selective $A_{2A}$ receptor deletions on bone formation at the site of wear particle-induced osteolysis will be examined using Xenolight Rediject Bone Probe 680 with scanning and quantitation of fluorescence in the IVIS apparatus. As can be seen in FIG. 1, this fluorophore, which binds to hydroxyapatite has been used to determine dynamic bone formation over time in mice without having to sacrifice the mice at any of the timepoints. This technique permits accurate assessment of bone formation while reducing the number of animals required to determine bone formation over time. All conditions will be tested in groups of five animals and repeated at least once. This number of mice has been sufficient to detect differences between treatment groups in the osteolysis model (Mediero, et al., *Sci Transl Med*, 2012. 4(135): 135-65).

Results.

In these experiments the effect of selective $A_{2A}$ receptor deletions on osteolysis will be determined in a murine model of wear particle-induced bone resorption, as we have previously reported (Mediero, et al., *Sci Transl Med*, 2012. 4(135): 135-65). Selective deletion of the $A_{2A}$ receptor in myeloid cells will diminish $A_{2A}$ receptor-mediated suppression of osteolysis by virtue of its effects on both the inflammatory cells and the osteoclasts present at the site of wear particle deposition. However, suppression of osteolysis in mice lacking $A_{2A}$ receptor expression in myeloid cells will not differentiate between invading inflammatory cells (macrophages) and osteoclasts since both cell types are of myeloid origin. Thus, the effect of selective $A_{2A}$ receptor deletion in osteoclasts will be examined to further differentiate whether osteoclasts or myeloid cells (or both) are involved. The interpretation of experiments carried out in the selective knockouts in osteoclasts should be more straightforward; an absence of $A_{2A}$ receptor agonist-mediated suppression of wear particle-mediated osteolysis in $A_{2a}$(flox/flox)×TRAP-cre mice would indicate that $A_{2A}$ receptor ligation on osteoclasts is sufficient to suppress wear particle-mediated osteolysis although this would not rule out a contribution from the inflammatory cells. In contrast, if CGS21680 inhibits osteolysis in $A_{2a}$(flox/flox)×TRAP-Cre mice it would suggest that the principal effect of suppression of osteolysis is mediated by inhibition of inflammatory cell function or osteoblast function. To determine the role of osteoblasts and adenosine receptor regulation of osteoblast function in suppressing osteolysis, the effect of osteoblast-selective deletion of $A_{2A}$ receptors on osteolysis will be determined and the expression of osteoblast mediators (e.g. RANKL) as well. If osteoblast-selective deletion abrogates $A_{2A}$ receptor ligation-mediated inhibition of osteolysis it will be clear that osteoblasts, presumably via expression of RANKL, play a critical role in osteolysis and the $A_{2A}$ receptor-mediated inhibition of osteolysis depends, at least in part, on suppression of osteoblast functions like production of RANKL.

Example 3

Examine the Molecular Mechanism by which $A_{2A}$ Receptor Stimulation Regulates Osteoblast and Osteoclast Function $A_{2A}$ receptor stimulation regulates a number of molecules that play a role in inflammation and communication between osteoclasts and osteoblasts thereby diminishing osteolysis.

Background

A variety of molecules mediate interactions between osteoclasts and osteoblasts, and these molecules play a role in osteolysis as well as protection from osteolysis by $A_{2A}$ receptor stimulation. For example, the inflammatory cells in the infiltrate associated with wear particles express sema4D, a molecule which suppresses osteoblast differentiation and bone formation. Similarly, $A_{2A}$ receptor stimulation increases plexin A1 expression on osteoclasts (the receptor for sema3B). Based on preliminary studies (microarray, in vitro studies and immunohistochemistry) a series of molecules which are known to, or are likely to, play a role in regulating bone remodeling and formation were identified at osteolytic sites. Moreover, expression of some of these proteins is also regulated by $A_{2A}$ receptor ligation. Among these molecules are RANKL ($A_{2A}$ receptor ligation inhibits osteoblast expression of RANKL, FIG. 2), sema4D ($A_{2A}$ receptor ligation inhibits osteoclast expression of sema4D and accumulation of inflammatory cells expressing sema4D, FIG. 3), plexin A1

(a co-receptor for sema3A on osteoclasts), netrin-1 and its receptor Unc5b ($A_{2A}$ receptor stimulation inhibits netrin-1 and Unc5b expression, FIG. 4). $A_{2A}$ receptor-mediated changes were screened for in other axonal guidance proteins either in vitro or in vivo and the neurotrophins nerve growth factor (NGF), brain-derived neurotrophic factor (BDNF) and neurotrophin-3 and their receptors TrkA, B and C may also drive osteoblast function as well. Clear evidence for direct activation of neurotrophin receptors by $A_{2A}$ receptors has been shown (Assaife-Lopes, et al., *J Neurosci,* 2010, 30(25): 8468-80; Lee, et al., *Proc Natl Acad Sci USA,* 2001, 98(6): 3555-60; Lee, et al., *Cytokine Growth Factor Rev,* 2002, 13(1): 11-17; Lee, et al., *Brain Research. Molecular Brain Research,* 2003, 111(1-2): 61-73 and Wiese, et al., *Proc Natl Acad Sci USA,* 2007, 104(43): 17210-5).

Stimulation of $A_{2A}$ receptors up-regulates osteoclast plexin A1 expression and inhibits sema4D and netrin-1 expression by osteoclasts and RANKL expression by osteoblasts both in vitro and in vivo. Netrin-1 heterozygous knockout bone marrow cells form significantly fewer osteoclasts in culture and $A_{2A}$ receptor stimulation inhibits netrin-1 production by osteoclast precursors from wild-type C57B1/6 mice as well as their expression of netrin-1's receptor unc5b (FIG. 4). Preliminary studies using an expression array for axonal guidance proteins previously indicate that the molecules chosen here are expressed in the cells of interest and indicates that the molecules chosen regulate osteoclast/osteoblast function or interactions. Thus, a discrete set of proteins (and animals) was chosen to study.

Materials and Methods.

A small set of axonal guidance proteins regulates osteoclast/osteoblast interactions, are expressed in bone cells at sites of wear particle-induced inflammation and osteolysis and are regulated by $A_{2A}$ receptors. These axonal guidance proteins and neurotrophins, which are regulated by $A_{2A}$ receptors in inflammatory cells, osteoclasts and osteoblasts, play a role in wear particle-induced osteolysis. A combination of knockout mice, cell specific-deletion of protein expression and radiation chimeras in a murine calvarial model of wear particle-induced osteolysis will be used. Murine models that are available include: netrin-1+/− mice and netrin-1$^{-/-}$ radiation bone marrow chimeras, sema4D knockout mice (heterozygotes were recently re-derived into our animal facility and we are now breeding homozygotes on a C57B1/6 background). In addition, RANKL (tnfsfl1) floxed mice will be available and will be bred with the osteoblast specific cre mice (Col 2.3 cre mice). The NIH has supported generation of plexin A1 deficient ES cells suitable for microinjection and generation of deficient mice. Using the services of the MMRC, an NIH-supported service these chimeric mice will be bred onto a suitable background (C57Black/6 background) for development of knockout mice and generation of bone marrow chimera mice. Appropriate mice with NGF, BDNF and TrkA, B and C mutations are available.

If deletion or diminished expression of any or all of these proteins diminishes osteolysis, the involvement of the $A_{2A}$ receptor-mediated regulation of the protein of interest will be investigated by injecting recombinant murine proteins into the air pouch of mice treated with $A_{2A}$ receptor agonists. The concentration of proteins to be injected into the air pouch will be determined empirically as the rate of catabolism and the concentrations required to promote osteolysis is not clear.

These experiments involve induction of wear particle-induced osteolysis in the murine calvarial model, as has been previously described (Mediero, et al., *Sci Transl Med,* 2012. 4(135): 135-65), in these mutant mice. The effect of local injection of an $A_{2A}$ receptor agonist into the air pouch overlying the particles with injection of vehicle (saline) in WT mice and in the knockouts, radiation chimeras and cell specific deletion (cre/lox) mice as well as reversal of $A_{2A}$ receptor-mediated inhibition of osteolysis will be investigated. The endpoints will be microCT assessment of porosity, histology and immunohistochemistry, cytokine production and dynamic bone formation (Xenolight Rediject Bone Probe 680 fluorescence in the affected area).

Results.

The results will be straightforward. If specific molecules are not involved in the pathogenesis of wear particle-induced osteolysis then there will be no reduction of osteolysis and, conversely, if a molecule is directly involved in osteolysis then diminished osteolysis will be observed. Demonstration that suppression of one or another protein by $A_{2A}$ receptor-stimulation plays a role in $A_{2A}$ receptor-mediated suppression of osteolysis can be inferred from these experiments. Nonetheless, it is likely that more than one of the target proteins will be involved in $A_{2A}$ receptor-mediated suppression of wear particle-induced osteolysis and thus we expect to observe diminution of osteolysis in mice mutated for a number of molecules.

Example 4

Dissect Intracellular Signaling Mechanisms by which Wear Particles Induce and $A_{2A}$ Receptor Stimulation Regulates Expression of RANKL, Sema4D, Plexin A1 and Netrin-1 in Osteoblasts and Osteoclasts Ingestion of particulates by monocyte/macrophages induces expression of sema4D and netrin-1. $A_{2A}$ receptors mediate their effects on expression of axonal guidance proteins via activation of adenylate cyclase, increased cAMP, activation of PKA/Epac1/2 and subsequent signaling steps.

Materials and Methods.

Osteoclast differentiation is shaped by both phagocytosis of particulates by macrophages and cells of myeloid origin and the bone matrix although neither the adhesion molecules required nor the signaling mechanisms involved have been elucidated as yet (Crotti, et al., *J Cell Physiol,* 2011, 226(12): 3413-21; James, et al., *J Immunol,* 2010, 185(2): 1265-73 and Shen, et al., *Arthritis Res Ther,* 2006, 8(3): R70). Indeed, timing of particle phagocytosis dictates whether myeloid cells differentiate into macrophages or osteoclasts since particle phagocytosis diminishes expression of RANK and c-fms (James, et al., *J Immunol,* 2010, 185(2): 1265-73), the receptors for RANKL and M-CSF. Nonetheless, osteolysis clearly results from particle exposure and is mediated, in part, by osteoclast-mediated bone resorption. The effect of phagocytosis of wear particles on expression of axonal guidance proteins like netrin-1 and sema4D has not been studied. Previous studies have demonstrated that monocyte/macrophages express little netrin-1 until the cells are activated; in atherosclerotic plaques the putative activating stimulus is lipid in the plaque (van Gils, et al., *Nat Immunol,* 2012, 13(2): 136-43). Consistent with this observation, preliminary studies indicate that there is little netrin-1 expressed by osteoclast precursors but that osteoclast differentiation is associated with increased expression. More strikingly, netrin-1 expressing macrophages were abundant in the inflammatory infiltrate of mice with particulate-induced osteolysis but completely absent in the $A_{2A}$ receptor agonist-treated mice. It is likely that, similar to its effect in atherosclerosis, netrin-1 expression is associated with diminished macrophage exit from the inflamed site and the macrophages present contribute to the inflammation and bone destruction. Similarly sema4D expression is abundant in the inflammatory infiltrate of particulate-treated mice but monocyte/macrophages express little sema4D unless they are activated and little sema4D is expressed in the $A_{2A}$ agonist-treated mice (FIG. 3 and (Sierra, et al., *J Exp Med*, 2008, 205(7): 1673-85)). Previous studies demonstrate that $A_{2A}$ receptor stimulation diminishes neutrophil and monocyte/macrophage phagocytosis as well although the downstream events have not been elucidated (Reviewed in (Milne, et al., *The Scientific World Journal*, 2011, 11: 320-339)). These findings suggest that $A_{2A}$ receptor ligation alters the osteoclast precursor's interactions with bone surface and secondarily diminishes osteoclast differentiation.

Figure 5:
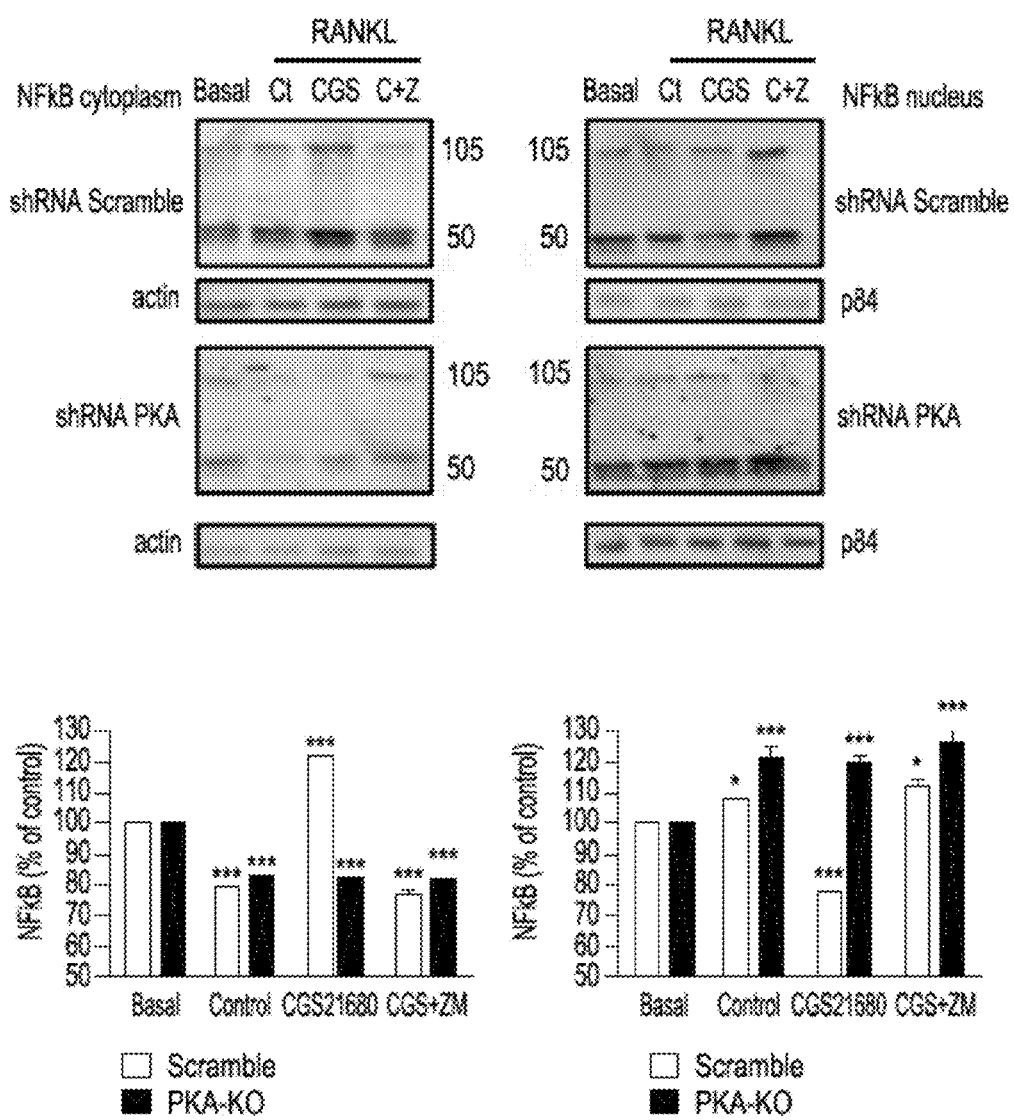
FIG. 5 demonstrates that $A_{2A}$ receptor activation inhibits NFκB p50/p105 nuclear translocation by a PKA-ERK1/2 mechanism. RAW264.7 cells were infected with lentiviral constructs expressing shRNA for the catalytic subunit of PKA or a scrambled control. Cells were incubated for 30 min in the presence of RANKL alone, plus CGS21680 (1 µM, CGS) or plus CGS and ZM241385 (1 µM, C+Z) before lysis, separation of nuclear and cytosolic fractions and analysis by Western Blot. Shown are representative Western Blots. Results in the bar graphs are expressed as the means of four independent experiments analyzed densitometrically and normalized to actin. Results were analyzed by two way ANOVA and Bonferroni post-hoc testing.

$A_{2A}$ receptors are members of the large family of G protein coupled receptors that signal via $G\alpha_S$ and cAMP. These receptors inhibit osteoclast differentiation in vitro although the intracellular signaling mechanisms that regulate this process are not fully established. Prior work has indicated that both PKA and EPAC activation inhibit osteoclast differentiation without affecting transcription of proteins involved in osteoclast differentiation (Granholm, et al., *J Endocrinol*, 2007, 195(3): 415-27). In other studies it has been reported that $A_{2A}$ receptor stimulation induces sumoylation of IκB and stabilization of the molecule with downstream inhibition of NFκB translocation in non-bone cells (Liu, et al., *J Biol Chem*, 2009, 284(20): 13686-95). The role of cAMP/protein kinase A (PKA) in the molecular regulation of osteoclast differentiation is being investigated. It has been shown that $A_{2A}$ receptors signal for inhibition of sema4D via PKA (FIG. 3) and $A_{2A}$ receptors signal for inhibition of NFκB translocation to the nucleus via cAMP-PKA since $A_{2A}$ receptor stimulation of RAW264.7 cells infected with a lentiviral vector expressing shRNA for the catalytic subunit of PKA does not prevent translocation of NFκB to the nucleus (FIG. 5). Moreover, stimulation of $A_{2A}$ receptors leads to activation of erk1/2 by a PKA-dependent mechanism (Not shown). In contrast to sema4D, $A_{2A}$ receptor stimulation inhibits netrin-1 expression by a PKA-independent mechanism since the effect of $A_{2A}$ receptor stimulation on netrin-1 expression is similar in scrambled and PKA catalytic subunit knock down RAW264.7 cells (Not shown). Increased intracellular cAMP levels also activate EPAC1/2, guanine nucleotide exchange factors (GEFs), which activate rap1, a GTPase generally associated with activation of the cytoskeleton. Results of recent studies using cAMP analogues selective for activation of Epac indicate that Epac activation also inhibits osteoclast differentiation (Granholm, et al., *J Endocrinol*, 2007, 195(3): 415-27). Thus, we will determine whether the effects of $A_{2A}$ receptor stimulation on osteoclast function are mediated by PKA/erk1/2 or Epac1/2 signaling.

Figure 2A:
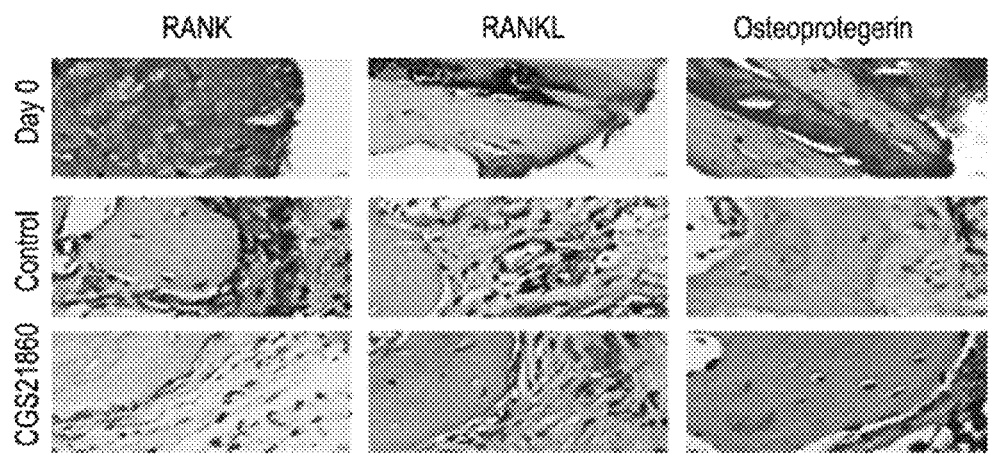
FIG. 2 demonstrates that adenosine $A_{2A}$ receptor ligation diminishes RANK, RANKL and increases osteoprotegerin expression in a murine model of wear particle-induced osteolysis and diminishes RANKL mRNA in differentiating osteoblasts. A. Shown are representative sections (from 10 different mice) of mouse calvarium after formation of an air pouch alone (sham) or after formation of an air pouch and exposure to wear particles for 4 weeks in the presence of saline or saline containing CGS21680 (1 µM), as we have previously described (Mediero, et al., Sci Transl Med, 2012. 4(135): 135-65). Dark brown staining is positive. B. RNA was isolated from normal human osteoblasts (Alizarin Red+/Alkaline Phosphatase+ cells) after differentiation from normal marrow cells in the presence or absence of CGS21680 (1 µM). Real time RT-PCR was carried out for RANKL and normalized to GAPDH. Shown are mean (+/−SD) results of two different samples carried out in duplicate.
Figure 2B:
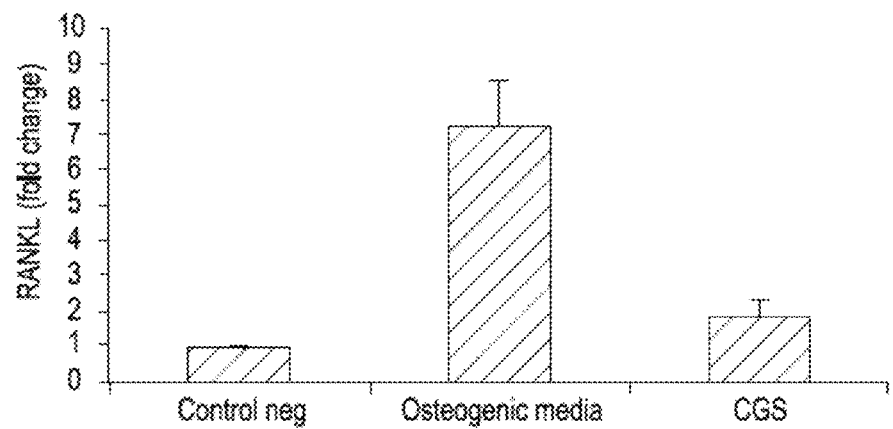
Figure 3A:
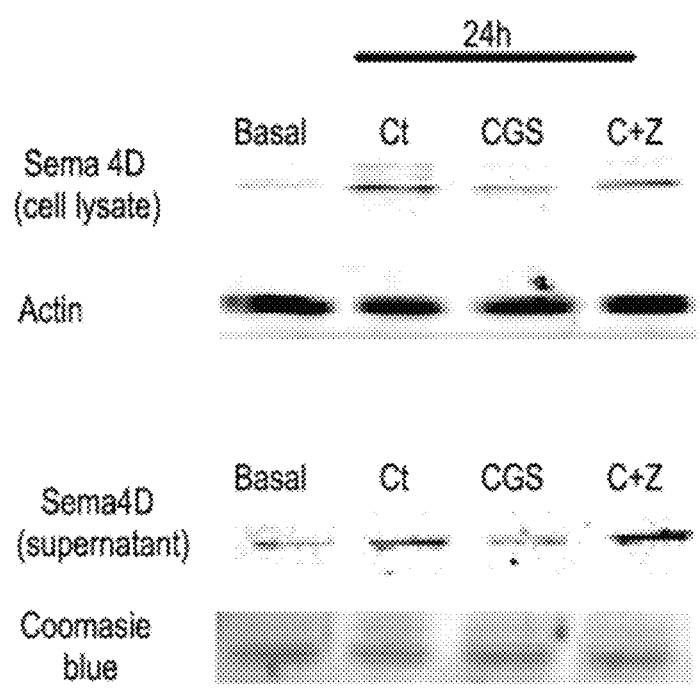
FIG. 3 demonstrates that adenosine $A_{2A}$ receptor stimulation inhibits, in a protein kinase A-dependent manner, semaphorin 4D expression by osteoclasts, diminishes recruitment of semaphorin 4D positive cells in a murine model of wear particle-induced osteolysis and is expressed in tissue recovered following prosthesis revision in patients. A.) Total cell lysates from primary murine bone marrow cells alone (basal) or after osteoclast differentiation in the presence of saline, CGS21680 (1 µM) with/without ZM241385 (1 µM) were subject to Western Blot detection of sema4D. Shown is a representative experiment of 3. B.) RAW264.7 osteoclasts, infected with a lentiviral vector expressing either shRNA for the catalytic subunit of PKA, scrambled shRNA, or primary murine bone marrow cells were cultured in the presence of saline (Black line) or CGS21680 (1 µM, Red Line) with/ without ZM241385 (1 µM, Blue Line) for the time periods indicated before harvest of the cells, collection of RNA and real time RTPCR. Results represent the means (±SEM) of 5 separate determinations. C. Calvarium from sham or wear particle-treated wild type (C57B1/6) mice or adenosine $A_{2A}$ receptor knockout mice (C57B1/6 background) were stained for sema4D. D. Soft tissue from patients stained for semaphorin 4D (original magnification 800×). On the left is soft tissue obtained at the time of joint replacement (Representative of 14). On the right is tissue obtained at time of prosthesis revision (representative of 12).
Figure 3B:
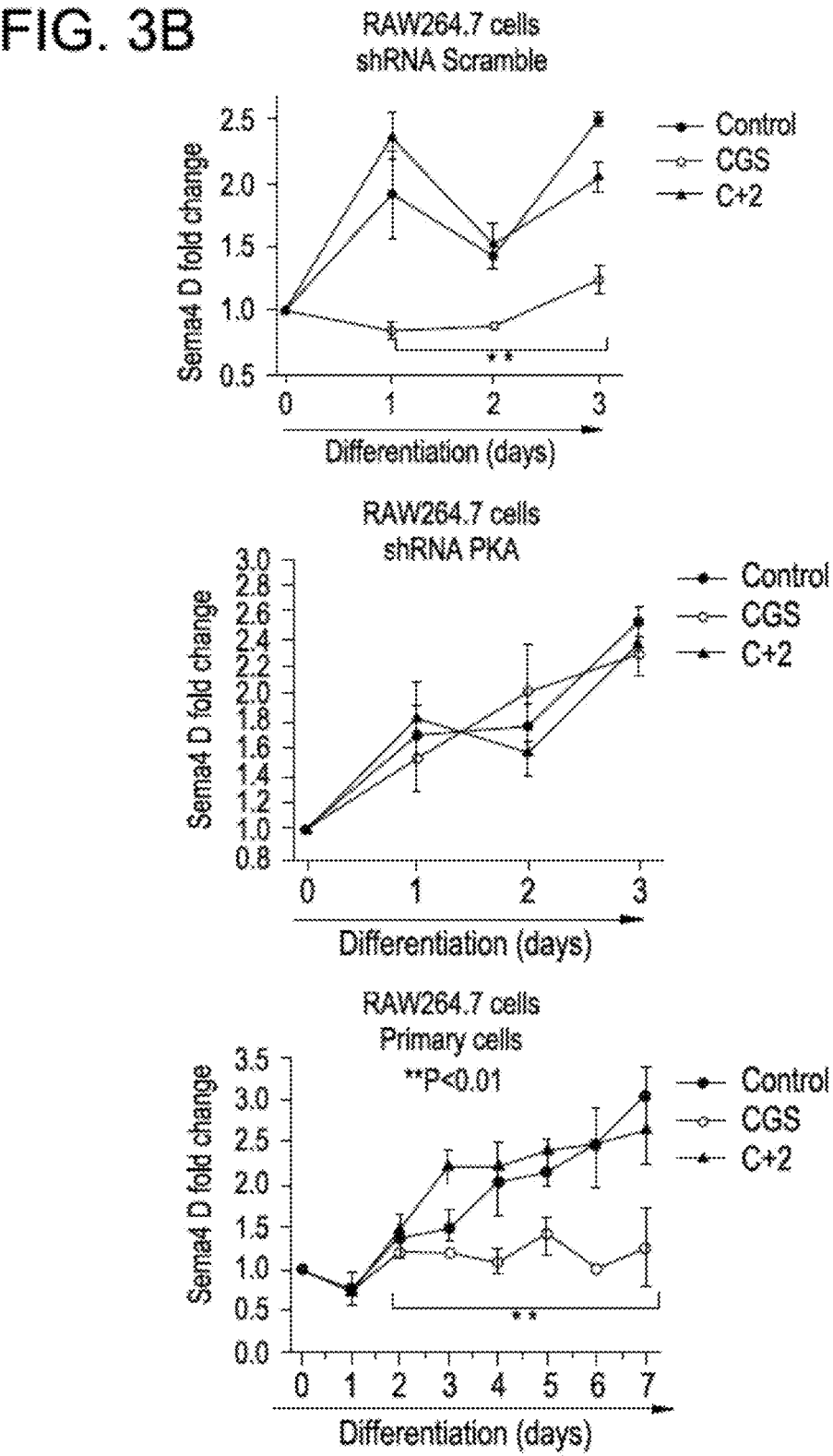
Figure 3C:
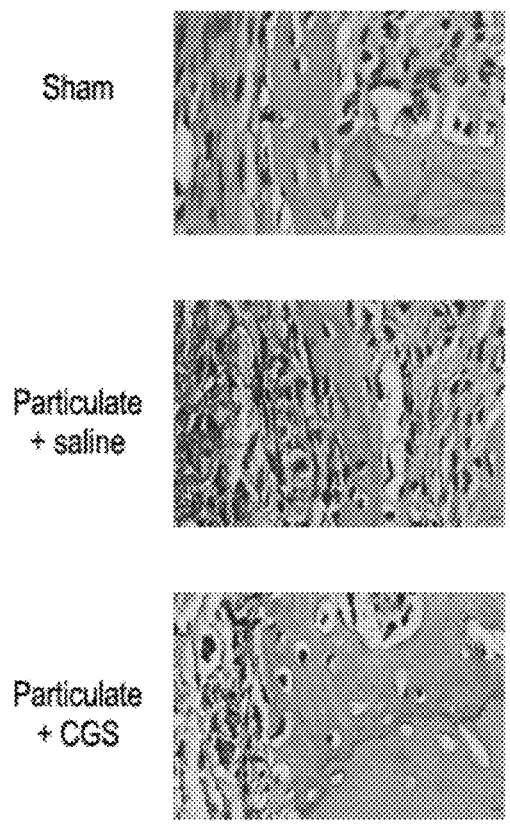
Figure 3D:
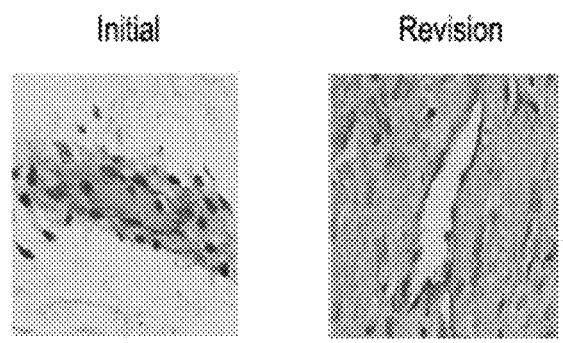
Figure 4A:
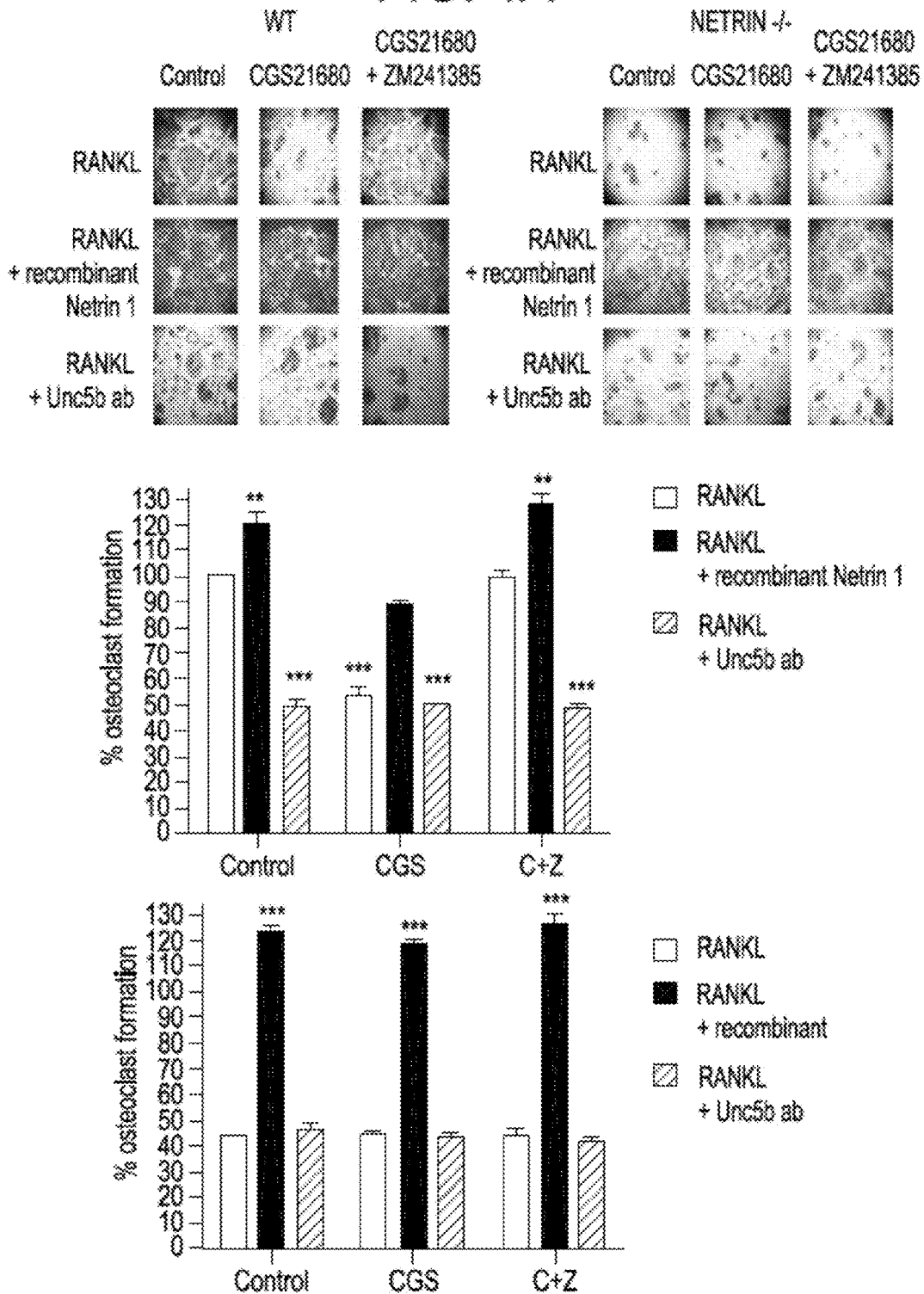
FIG. 4 demonstrates that netrin-1 expression by osteoclasts is regulated by adenosine $A_{2A}$ receptor stimulation, is required for osteoclast formation and is expressed in periosteal inflammatory tissue at sites of osteolysis in mice and patients undergoing prosthesis revision. A.) Bone marrow cells from WT and radiation chimeric netrin$^{-/-}$ bone marrow mice were isolated and induced to differentiate into osteoclasts by incubation with RANKL and M-CSF. The netrin$^{-/-}$ cells did not differentiate into TRAP$^+$ osteoclasts, an effect reversed by recombinant netrin-1. The $A_{2A}$ receptor agonist CGS21680 (1 µM) reduces osteoclast differentiation in WT cells and the effect is reversed by both netrin-1 (250 ng/ml) and by the $A_{2A}$ antagonist ZM241385. Cells from 5 different mice repeated in duplicate. B. Western blot analysis reveals that CGS21680 (1 µM) reduces netrin-1 in the supernate of RAW264.7 cells induced to undergo differentiation to osteoclasts by RANKL and M-CSF. $A_{2A}$ receptor stimulation reduces Unc5b, but not DCC, expression. Representative of 2 experiments. C. Bone mineral density (BMD) determined by Pixamouse small animal Dexa scanner. WT mice and Netrin1 KO mice are chimeras generated by infusion of either normal or netrin-1 deficient fetal liver into lethally irradiated congenic C57Black/6 mice. BMD was measured 18 weeks after transplant. Shown are the results of determinations on 5 mice in each group. D. Netrin-1 expression is increased in the inflammatory infiltrate in wear particle-induced osteolysis and $A_{2A}$ receptor stimulation inhibits its expression. Representative of 5 different mice with each treatment. E. Soft tissue from patients stained for semaphorin 4D (original magnification 800×). On the left is soft tissue obtained at the time of hip replacement (Representative of 14). On the right is tissue obtained at the time of hip replacement (representative of 14). On the right is tissue obtained at time of prosthesis revision (representative of 12).
Figure 4B:
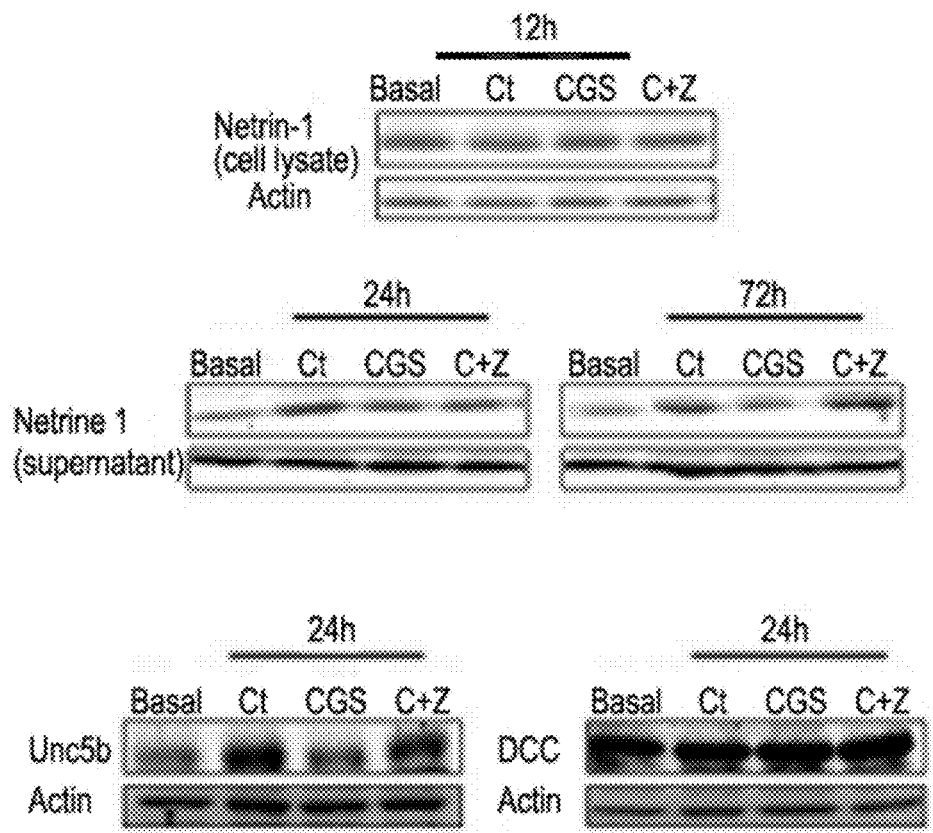
Figure 4C:
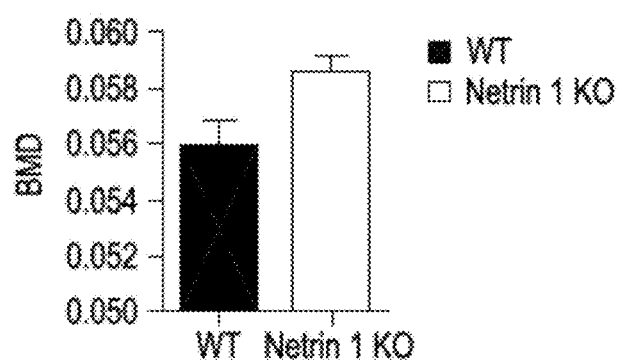
Figure 4D:
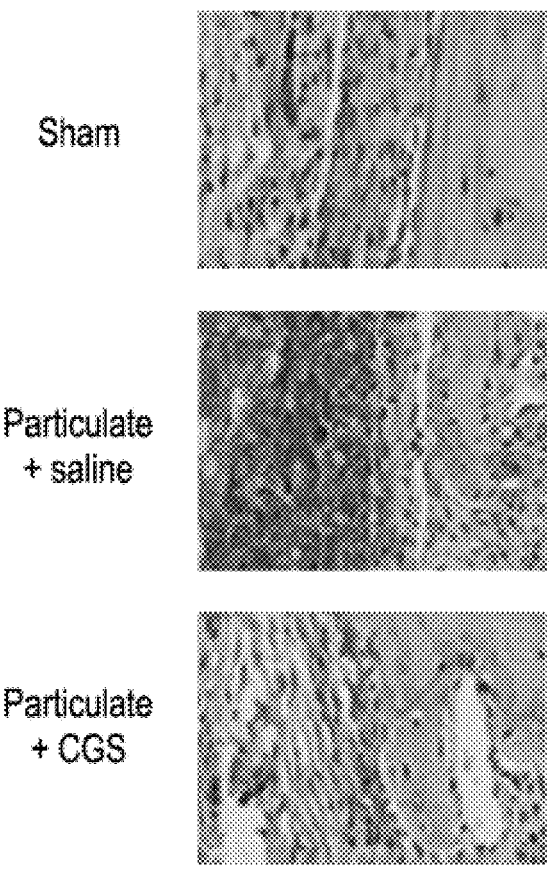
Figure 4E:
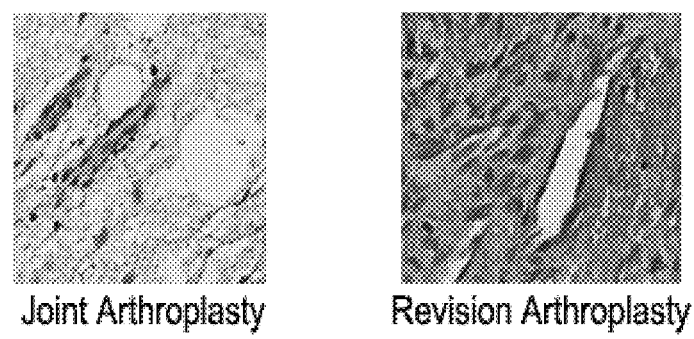

$A_{2A}$ receptor stimulation selectively inhibits primary human osteoblast expression of RANKL without affecting osteoblast differentiation (FIG. 2). It was previously reported that adenosine $A_{2B}$ receptor stimulation inhibited osteoprotegerin secretion by HCC1 cells and primary human bone marrow cells (Evans, et al., *J Bone Miner Res*, 2006, 21(2): 228-36). In contrast, $A_{2A}$ receptor stimulation was without effect on expression of osteoprotegerin. It was noted that HCC1 cells express very low levels of RANKL mRNA or protein and there was no adenosine receptor-mediated suppression of RANKL expression. Nonetheless, previous studies in osteoblasts indicate that stimulation of osteoblasts and osteoblast precursors with PTH stimulates expression of RANKL by a cAMP/PKA/CREB signaling cascade (Fu, et al., *Mol Cell Biol*, 2006, 26(17): 6453-68). Moreover, RUNX2 overexpression enhances the effect of CREB signaling on RANKL expression (Fu, et al., *Mol Cell Biol*, 2006, 26(17): 6453-68) although in preliminary studies we have observed that $A_{2A}$ receptor stimulation does not affect RUNX2 expression in osteoblasts (Not shown). In addition, adenosine, acting at A2BAR (also a $G\alpha_S$-linked protein that signals via cAMP cascades), promotes osteoblast differentiation (Russell, et al., *Calcif Tissue Int*, 2007, 81(4): 316-26; Evans, et al., *J Bone Miner Res*, 2006, 21(2): 228-36 and Carroll, et al., *J Biol Chem*, 2012, 287(19): 15718-27). Thus, the effects of cAMP and cAMP-stimulating agents seem somewhat contradictory in these cells.

Materials and Methods.

This experiment will have three components, examination of the effect of particle phagocytosis on sema4D, netrin-1, Unc5b and plexinA1 on primary murine macrophages (resting and thioglycollate-induced peritoneal macrophages), RAW264.7 cells and primary human monocytes and THP-1 cells (a human cell line that differentiates into macrophages) and the effect of $A_{2A}$ receptor stimulation on both particle phagocytosis and expression of these molecules. In addition $A_{2A}$ receptor signaling in osteoclasts (both primary and RAW264.7 cells induced to undergo osteoclast differentiation) will be examined with complementary studies in osteoblasts.

The initial approach will be to determine whether phagocytosis of wear particles directly regulates expression of the molecules of interest (mRNA and protein by ELISA or Western Blot). The effect of an $A_{2A}$ receptor agonist/antagonist on particle phagocytosis (number of particles, % of cells phagocytosing particles) and expression of the proteins of interest, as above, will be examined. The next studies will examine $A_{2A}$ receptor signaling in macrophage/monocytes and osteoclasts, primary murine macrophages (resting and thioglycollate-induced peritoneal macrophages) and human monocytes as well as primary murine and human osteoclasts and RAW264.7 cells induced to differentiate into osteoclasts with RANKL (Kara, et al., *Arthritis Rheum*, 2010, 62(2): 534-41; Kara, et al., *FASEB J*, 2010, 24(7): 2325-33; He, et al., *Purinergic Signal*, 2012, 8(2): 327-37; Mediero, et al., *Am J Pathol*, 2012, 180(2): 775-86; Crotti, et al., *J Cell Physiol*, 2011, 226(12): 3413-21; James, et al., *J Immunol*, 2010, 185(2): 1265-73 and Shen, et al., *Arthritis Res Ther*, 2006, 8(3): R70). Once it is shown that pharmacologic inhibitors of signaling molecules block the effects of $A_{2A}$ receptor stimulation on expression of a specific molecule by primary cells and RAW264.7 cells the remainder of the experiments will be performed in RAW264.7 cells as we have strong experience knocking down signaling molecules (Bingham, et al., *J Leukoc Biol*, 2010, 87(4): 683-90) by use of lentiviral vectors and shRNA with puromycin selection (scrambled shRNA as a control, cf FIG. 3, (Bingham, et al., *J Leukoc Biol*, 2010, 87(4): 683-90 and Bingham, et al., *Inflammation*, 2012, 35(1): 49-57)). Thus the data will demonstrate that $A_{2A}$ receptor expression inhibits expression of sema4D, netrin-1, Unc5b and plexin A1 on osteoclasts, as demonstrated by real time-QPCR and Western Blot analysis in osteoclast precursors from primary bone marrow and RAW264.7 cells as has been previously described (He, et al., *Purinergic Signal*, 2012, 8(2): 327-37 and Mediero, et al., *Am J Pathol*, 2012, 180(2): 775-86). PKA knockdown cells have been generated, and epac1/2 and erk1 and erk2 knockdown cells will be generated (transient transfection has also been used (Che, et al., *Mol Pharmacol*, 2007, 72(6): 1626-36)). To determine if $A_{2A}$ receptor activation inhibits NFκB translocation to the nucleus via increasing Iκb sumoylation sumoylation of IκB will be measured directly by immunoprecipitation with anti-SUMO antibodies followed by Western Blot analysis of precipitated proteins (for IκB), as previously described for $A_{2BA}$ receptor (Liu, et al., *J Biol Chem*, 2009, 284(20): 13686-95). These experiments will be carried out in PKA, erk1 and 2 knockdown cells to determine whether these proteins are involved in signaling downstream from $A_{2A}$ receptor activation leading to diminished NFκB nuclear translocation and, if positive, sumoylation of IκB. The activated signaling molecules or their activity will be quantified (e.g. erk1/2 phosphorylation, transcriptional assays, etc) as has been previously described in a number of other systems (He, et al., *Purinergic Signal*, 2012, 8(2): 327-37; Che, et al., *Mol Pharmacol*, 2007, 72(6): 1626-36; Peng, et al., *J Clin Invest*, 2009, 119(3): 582-94 and Peng, et al., *FASEB J*, 2008). Microarray analysis of mRNA in $A_{2A}$ receptor-stimulated and unstimulated macrophages will be carried out to better localize other signaling cascades that may be involved, as has been previously described (Crotti, et al., *J Cell Physiol*, 2011, 226(12): 3413-21 and Garrigues, et al., *Biomaterials*, 2005, 26(16): 2933-45).

In osteoblasts a similar approach will be employed. The action of $A_{2A}$ receptors on RANKL expression in primary human and murine osteoblast precursors and osteoblasts is similar to that observed in murine (MC3T3 cells) or human cell lines (e.g. HCC1 cells cannot be used for these experiments because they do not resemble primary osteoblast precursors with respect to RANKL expression). Similarly, the effect of pharmacologic stimuli/inhibitors of signaling molecules (PKA, Epac1/2, MAPKinases) will be tested to determine their effect on the capacity of $A_{2A}$ receptor stimulation to regulate osteoblast expression of RANKL and osteoprotegerin. When specific signaling molecules appear to be involved (reversal of $A_{2A}$ receptor effects by pharmacologic inhibitors, mimicking of effect by PKA- and Epac1/2-selective cAMP analogues) they will be knocked down using either lentiviral vectors with shRNA (scrambled shRNA as a control) or transient transfection and determine whether $A_{2A}$ receptor stimulation affects RANKL or osteoprotegerin expression. Finally, microarray experiments will be performed to determine if other signaling pathways are involved, as described above.

Results.

The results are quite straightforward to interpret. Using pharmacologic activators/inhibitors of specific signaling molecules, always recognizing the general limitation of inhibitors that they may not be as specific as the investigator thinks, one can narrow one's investigations to specific signaling cascades and molecules. Upon narrowing the scope of the experiments efforts may be concentrated on knocking down specific signaling molecules to further demonstrate their role in the signaling cascades in question. By use of this layered approach it is possible to identify the relevant signaling cascades regulating each of the molecules under study.

The invention claimed is:

1. A method for therapeutically inhibiting, reducing or slowing osteolysis comprising administering to a subject a therapeutically effective amount of an anti-netrin-1 antibody, and one or more other agents effective to inhibit bone resorption or differentiation or stimulation of osteoclasts.

2. The method according to claim 1 wherein the netrin-1 receptor is unc5b.

3. The method according to claim 1 wherein the one or more other agents are selected from the group consisting of an anti-inflammatory compound, a bisphosphonate and a growth factor.

4. A method for therapeutically inhibiting osteoclast differentiation, activation or activity comprising administering to a subject a therapeutically effective amount of an anti-netrin-1 antibody, and one or more other agents effective to inhibit bone resorption or differentiation or stimulation of osteoclasts.

5. The method according to claim 4 wherein the netrin-1 receptor is unc5b.

6. The method according to claim 4 wherein the one or more other agents are selected from the group consisting of an anti-inflammatory compound, a bisphosphonate and a growth factor.

7. A method for therapeutically increasing or promoting bone density comprising administering to a subject a therapeutically effective amount of an anti-netrin-1 antibody, and one or more other agents effective to inhibit bone resorption or differentiation or stimulation of osteoclasts.

8. The method according to claim 7 wherein the netrin-1 receptor is unc5b.

9. The method according to claim 7 wherein the one or more other agents are selected from the group consisting of an anti-inflammatory compound, a bisphosphonate and a growth factor.

10. A method for therapeutically treating a disease caused all or in part by or characterized by osteolysis, reduced bone density or undesired osteoclast activity comprising administering to a subject a therapeutically effective amount of an anti-netrin-1 antibody.

11. The method according to claim 10 wherein the disease is selected from the group consisting of osteoporosis, an inflammatory disease of bone, a metabolic bone disease, a metastatic bone disease, and multiple myeloma.

12. The method according to claim 10 further comprising inhibiting osteoclast differentiation, activation or activity.

13. The method according to claim 10 further comprising stimulating osteoblast differentiation, activation or activity.

14. The method according to claim 10 wherein netrin-1 receptor is unc5b.

15. The method according to claim 10 further comprising administering one or more other agents effective to inhibit bone resorption or differentiation or stimulation of osteoclasts.

16. The method according to claim 15 wherein the one or more other agents are selected from the group consisting of an anti-inflammatory compound, a bisphosphonate and a growth factor.

* * * * *